United States Patent [19]
Benaron et al.

[11] Patent Number: 5,762,609
[45] Date of Patent: Jun. 9, 1998

[54] DEVICE AND METHOD FOR ANALYSIS OF SURGICAL TISSUE INTERVENTIONS

[75] Inventors: David A. Benaron, Redwood City, Calif.; Daniel S. Goldberger, Boulder, Colo.; David E. Goodman, San Francisco; Robert S. Smith, Berkeley, both of Calif.

[73] Assignee: Sextant Medical Corporation, Boulder, Colo.

[21] Appl. No.: 474,263

[22] Filed: Jun. 7, 1995

Related U.S. Application Data

[63] Continuation-in-part of Ser. No. 944,516, Sep. 14, 1992, Pat. No. 5,460,182, Ser. No. 437,327, May 9, 1995, and Ser. No. 24,278, Feb. 26, 1993.

[51] Int. Cl.$^6$ ...................................................... A61B 6/00
[52] U.S. Cl. ................................ 600/473; 600/476; 606/34
[58] Field of Search ............................. 128/664, 665, 128/633, 653.1; 607/2, 96–102; 606/27–31, 32–34, 49; 600/473, 476, 310, 342, 567

[56] References Cited

U.S. PATENT DOCUMENTS

| | | | |
|---|---|---|---|
| 2,437,916 | 3/1948 | Greenwald | 128/2 |
| 3,674,008 | 7/1972 | Johnson | 128/2 A |
| 3,847,483 | 11/1974 | Shaw et al. | 356/41 |
| 3,941,121 | 3/1976 | Olinger et al. | 128/6 |
| 3,961,621 | 6/1976 | Northeved | 128/2 B |

(List continued on next page.)

FOREIGN PATENT DOCUMENTS

| | | | |
|---|---|---|---|
| 3920706 | 1/1991 | Germany | 600/182 |
| 0 017 108 | 10/1992 | WIPO | 128/634 |

OTHER PUBLICATIONS

Edholm et al., "Tissue Identification During Needle Puncture By Reflection Spectrophotmetry", Med & Biol Engng, vol. 6, pp. 409–413 (1968).

Talamini et al., "Laproscopic Equipment and Instrumentation", Chapter 2, Surgical Laparoscopy (Zucker ed), (1991) pp. 23–27, 35–36, 40–55.

"Instrumentation" Laparoscopic Complication (1991) pp. 5–13.

Edholm et al., "Detection of Aortic Atheromatosis In Vivo By Reflection Spectrophotometry", J. Atheroscler. Res. 5, (1965).

Polanyi In Vivo Oximeter With Fast Dynamic Response, The Review of Scientific Instruments, vol. 33, No. 10, 1962, pp. 1050–1054.

Benaron, "2D and 3D Images of Thick Tissue . . . ", SPIE 1641: 35–45 (1992).

Benaron, "Imaging (NIRI) and quantitation (NIRS) In Tissue . . . ", SPIE 1888: 10–21, Jan. (1993).

Benaron et al., "Optical Time–Of–Flight and Absorbance Imaging Of Biologic Medic", Science, (1993) 259: 1463–1466.

J.S. Wyatt et al., "Measurement of Optical Path Length for Cerebral Near–Infrared Spectroscopy in Newborn Infants", Dev Neuroscci 1990; 12:140–144.

Howard Mark, Chemometrics In Near–Infrared Spectroscopy, Analytica Chimica Act, 223 (1989), pp. 75–93.

D. Benaron et al., "Non–Invasive Estimation of Cerebral Oxygenation and Oxygen Consumption Using Phase–Shift Spectrophotometry", Proceedings of the Twelfth Annual International Conference of the IEEE Engineering in Medicine and Biology Society, vol. 12: No. 5, 1990, pp. 2004–2006.

(List continued on next page.)

Primary Examiner—Brian L. Casler
Attorney, Agent, or Firm—Orrick, Herrington & Sutcliffe

[57] ABSTRACT

A class of novel surgical tools constructed from the surgical tools and a tissue state monitoring device to assess or image changes in the chemical or structural composition of tissue over time, which give feedback to surgeons during dynamic surgical interventions that change the character of tissue, such as tissue welding.

62 Claims, 10 Drawing Sheets

5,762,609
Page 2

U.S. PATENT DOCUMENTS

| | | | |
|---|---|---|---|
| 3,963,019 | 6/1976 | Quandt | 128/2 T |
| 4,085,756 | 4/1978 | Weaver | 128/303.17 |
| 4,190,053 | 2/1980 | Sterzer | 607/96 |
| 4,191,191 | 3/1980 | Auburn | 128/347 |
| 4,269,192 | 5/1981 | Matsuo | 128/665 |
| 4,290,433 | 9/1981 | Alfano | 128/665 |
| 4,295,470 | 10/1981 | Shaw et al. | 128/634 |
| 4,299,230 | 11/1981 | Kubota | 128/630 |
| 4,311,138 | 1/1982 | Sugarman | 128/214.4 |
| 4,322,164 | 3/1982 | Shaw et al. | 356/243 |
| 4,350,148 | 9/1982 | Sivak Jr. et al. | 128/4 |
| 4,356,682 | 11/1982 | Kubota | 128/630 |
| 4,380,240 | 4/1983 | Jobsis | 128/633 |
| 4,410,020 | 10/1983 | Lorenz | 141/65 |
| 4,416,285 | 11/1983 | Shaw et al. | 128/634 |
| 4,421,106 | 12/1983 | Uehara | 128/4 |
| 4,448,194 | 5/1984 | DiGiovanni et al. | 128/334 R |
| 4,471,781 | 9/1984 | DiGiovanni et al. | 128/334 R |
| 4,502,487 | 3/1985 | Dubrucq et al. | 128/665 |
| 4,509,368 | 4/1985 | Whiting | 73/624 |
| 4,527,569 | 7/1985 | Kolb | 128/660 |
| 4,532,935 | 8/1985 | Wang | 128/753 |
| 4,539,586 | 9/1985 | Danna et al. | 358/98 |
| 4,555,179 | 11/1985 | Langerhole et al. | 356/237 |
| 4,566,438 | 1/1986 | Liese et al. | 128/6 |
| 4,601,710 | 7/1986 | Moll | 604/165 |
| 4,607,621 | 8/1986 | Wheeler | 600/110 |
| 4,617,940 | 10/1986 | Wang | 128/753 |
| 4,622,974 | 11/1986 | Coleman et al. | 128/634 |
| 4,633,885 | 1/1987 | DuBrucq | 128/736 |
| 4,650,327 | 3/1987 | Ogi | 356/243 |
| 4,658,825 | 4/1987 | Hochberg et al. | 128/634 |
| 4,667,229 | 5/1987 | Cooper et al. | 358/9 |
| 4,682,585 | 7/1987 | Hilterbrandt | 128/4 |
| 4,759,348 | 7/1988 | Cawood | 600/104 |
| 4,763,662 | 8/1988 | Yokoi | 128/660 |
| 4,765,736 | 8/1988 | Gallagher | 356/300 |
| 4,768,513 | 9/1988 | Suzuki | 607/99 |
| 4,773,097 | 9/1988 | Suzaki | 382/6 |
| 4,805,623 | 2/1989 | Jobsis | 128/633 |
| 4,810,875 | 3/1989 | Wyatt | 128/665 |
| 4,854,320 | 8/1989 | Dew et al. | 128/397 |
| 4,864,648 | 9/1989 | Kordts et al. | 455/608 |
| 4,872,187 | 10/1989 | Nakahata | 378/4 |
| 4,887,606 | 12/1989 | Yock et al. | 128/662.05 |
| 4,902,280 | 2/1990 | Lander | 604/165 |
| 4,910,404 | 3/1990 | Cho | 250/358 |
| 4,911,148 | 3/1990 | Sosnowaki et al. | 128/6 |
| 4,917,097 | 4/1990 | Proudian et al. | 128/662.06 |
| 4,930,516 | 6/1990 | Alfano et al. | 128/665 |
| 4,945,895 | 8/1990 | Takai et al. | 128/6 |
| 4,948,974 | 8/1990 | Nelson et al. | 128/664 |
| 4,951,677 | 8/1990 | Crowley et al. | 128/662.06 |
| 4,959,063 | 9/1990 | Kojima | 606/15 |
| 4,970,757 | 11/1990 | Heiland et al. | 452/140 |
| 4,972,827 | 11/1990 | Kishi et al. | 128/3 |
| 4,981,138 | 1/1991 | Deckelbaum et al. | 128/665 |
| 4,998,527 | 3/1991 | Meyer | 128/6 |
| 5,000,752 | 3/1991 | Hoskin et al. | 606/9 |
| 5,002,051 | 3/1991 | Dew et al. | 128/395 |
| 5,002,557 | 3/1991 | Hasson | 606/191 |
| 5,030,206 | 7/1991 | Lander | 604/164 |
| 5,030,207 | 7/1991 | Mersch et al. | 604/168 |
| 5,037,433 | 8/1991 | Wilk et al. | 606/139 |
| 5,053,016 | 10/1991 | Lander | 604/69 |
| 5,057,695 | 10/1991 | Hirao et al. | 250/575 |
| 5,066,288 | 11/1991 | Deniega et al. | 604/274 |
| 5,070,874 | 12/1991 | Barnes et al. | 128/664 |
| 5,078,712 | 1/1992 | Easley et al. | 606/16 |
| 5,088,493 | 2/1992 | Giannini et al. | 128/664 |
| 5,099,123 | 3/1992 | Harjunmaa | 250/339 |
| 5,100,402 | 3/1992 | Fan | 606/41 |
| 5,104,382 | 4/1992 | Brickerhoff et al. | 604/165 |
| 5,104,383 | 4/1992 | Shichman | 604/167 |
| 5,112,330 | 5/1992 | Nishigaki et al. | 606/46 |
| 5,114,407 | 5/1992 | Burbank | 604/164 |
| 5,116,353 | 5/1992 | Green | 606/184 |
| 5,119,815 | 6/1992 | Chance | 128/633 |
| 5,131,398 | 7/1992 | Alfano et al. | 128/665 |
| 5,137,355 | 8/1992 | Barbour et al. | 356/342 |
| 5,139,025 | 8/1992 | Lewis et al. | 128/665 |
| 5,140,984 | 8/1992 | Dew et al. | 128/395 |
| 5,140,989 | 8/1992 | Lewis et al. | 128/665 |
| 5,152,278 | 10/1992 | Clayman | 128/4 |
| 5,154,709 | 10/1992 | Johnson | 606/45 |
| 5,186,714 | 2/1993 | Boudreault et al. | 604/21 |
| 5,192,280 | 3/1993 | Parins | 606/48 |
| 5,197,964 | 3/1993 | Parins | 606/48 |
| 5,199,431 | 4/1993 | Kittrell et al. | 128/665 |
| 5,201,732 | 4/1993 | Parins et al. | 606/47 |
| 5,203,339 | 4/1993 | Knuttel et al. | 128/665 |
| 5,213,105 | 5/1993 | Gratton et al. | 250/341 |
| 5,217,458 | 6/1993 | Parins | 606/48 |
| 5,219,345 | 6/1993 | Potter | 128/665 |
| 5,250,047 | 10/1993 | Rydell | 606/48 |
| 5,258,006 | 11/1993 | Rydell et al. | 606/205 |
| 5,271,380 | 12/1993 | Riek et al. | 128/4 |
| 5,275,168 | 1/1994 | Reintjes et al. | 128/665 |
| 5,280,788 | 1/1994 | Janes et al. | 128/665 |
| 5,290,278 | 3/1994 | Anderson | 606/15 |
| 5,290,286 | 3/1994 | Parins | 606/50 |
| 5,300,065 | 4/1994 | Anderson | 606/13 |
| 5,312,400 | 5/1994 | Bales et al. | 606/41 |
| 5,318,023 | 6/1994 | Vari et al. | 128/634 |
| 5,324,289 | 6/1994 | Eggers | 606/48 |
| 5,330,471 | 7/1994 | Eggers | 606/48 |
| 5,352,222 | 10/1994 | Rydell | 606/37 |
| 5,352,223 | 10/1994 | McBrayer et al. | 606/51 |
| 5,423,321 | 6/1995 | Fontenot | 128/664 |
| 5,601,087 | 2/1997 | Gunderson et al. | 128/664 |

OTHER PUBLICATIONS

D. Benaron et al., "Optical Path Length of 754nm and 816nm Light Emitted Into the Head of Infants", Proceedings of the Twelfth Annual International Conference of the IEEE Engineering in Medicine and Biology Society, vol. 12., No. 3, 1990, pp. 117–119.

D. Benaron et al., "Tomographic Time–of–Flight Optical Imaging Scanner with Non–Parallel Ray Geometry, Non–Parallel Rotational Optical Tomography", *Applied Optics* (in press) pp. 2–33.

Nezhat et al., "Laparoscopic Removal of Dermoid Cysts", *Obstetrics & Gynecology*, vol. 73, No. 2, Feb. 1989, pp. 278–280.

Nezhat et al., "Laparoscopic radical hysterectomy with paraaortic and pelvic node dissection", *Am J Obstet Gynecol* 1992, 166:864–5.

Nezhat et al., "Salpingectomy via Laparoscopy, A New Surgical Approach", *Journal of Laparoendoscopic Surgery*, vol. 1, No. 2, 1991, pp. 91–95.

Nezhat et al., "Endoscopic Infertility Surgery", *Journal of Reproductive Medicine*, vol. 34, No. 2, Feb. 1989, pp. 127–134.

Nezhat et al., "Videolaseroscopy For Oophorectomy", *Am J Obstet Gynecol* 1991, 165:1323–30.

Nezhat et al., "Laparoscopic Versus Abdominal Hysterctomy", *Journal of Reproductive Medicine*, Vo 37, No. 3, Mar. 1992, pp. 247–250.

Nezhat et al., "Videolaseroscopy", *Obstetrics And Gynecology Clinics of North America*, vol. 18, No. 3, Sep. 1991, pp. 585–604.

Nezhat et al., "Operative Laparoscopy (Minimally Invasive Surgery), State of the Art", *J. Gynecol Surg.*, 8:111, 1992, pp. 111–141.

| EMITTER-DETECTOR PAIR MEASURED | DIST | ABS AT 325 | RATIO | NO BALL | SMALL BALL | LARGE BALL |
|---|---|---|---|---|---|---|
| 323A-324A | 1CM | 1.03 | 1.0 | NO | NO | NO |
| 323B-324B | 1CM | 1.05 | 1.1 | NO | NO | NO |
| 323C-324C | 1CM | 0.98 | 1.0 | NO | NO | YES |
| 323D-324D | 1CM | 0.95 | 1.0 | NO | NO | NO |
| 323E-324E | 1CM | 1.01 | 1.0 | NO | NO | NO |
| 323A-324B | 2CM | 2.04 | 1.0 | NO | NO | NO |
| 323B-324C | 2CM | 2.43 | 1.2 | NO | NO | YES |
| 323C-324D | 2CM | 4.53 | 2.2 | NO | YES | YES |
| 323D-324E | 2CM | 2.41 | 2.2 | NO | NO | YES |
| 323E-324F | 2CM | 2.38 | 2.2 | NO | NO | NO |
| 323A-324C | 3CM | 3.07 | 1.0 | NO | NO | YES |
| 323B-324D | 3CM | 6.01 | 2.0 | NO | YES | YES |
| 323C-324E | 3CM | 6.31 | 2.1 | NO | YES | YES |
| 323D-324F | 3CM | 3.10 | 1.0 | NO | NO | YES |
| 323A-324D | 4CM | 4.20 | 1.0 | NO | NO | YES |
| 323B-324E | 4CM | 8.80 | 2.2 | NO | YES | YES |
| 323C-324F | 4CM | 8.78 | 2.2 | NO | YES | YES |
| 323D-324G | 4CM | 3.98 | 1.0 | NO | NO | YES |

|   | 1 CM | 2 CM | 3 CM | 4 CM |
|---|------|------|------|------|
| A | NO   | NO   | —    | —    |
| B | NO   | YES  | YES  | YES  |
| C | YES  | YES  | YES  | YES  |
| D | NO   | YES  | YES  | YES  |
| E | NO   | NO   | YES  | YES  |

|   | 1 CM | 2 CM | 3 CM | 4 CM |
|---|------|------|------|------|
| A | NO   | NO   | —    | —    |
| B | NO   | NO   | NO   | NO   |
| C | NO   | YES  | YES  | YES  |
| D | NO   | NO   | YES  | YES  |
| E | NO   | NO   | NO   | NO   |

|   | 1 CM | 2 CM | 3 CM | 4 CM |
|---|------|------|------|------|
| A | NO   | NO   | —    | —    |
| B | NO   | NO   | NO   | NO   |
| C | NO   | NO   | NO   | NO   |
| D | NO   | NO   | NO   | NO   |
| E | NO   | NO   | NO   | NO   |

FIG. 7C

DEVICE AND METHOD FOR ANALYSIS OF SURGICAL TISSUE INTERVENTIONS

RELATED APPLICATIONS

This application is a continuation-in-part of commonly assigned U.S. patent application Ser. No. 07/944,516 filed Sep. 14, 1992 in the names of David E. Goodman and Daniel S. Goldberger and entitled TISSUE PENETRATING APPARATUS AND METHODS, now U.S. Pat. No. 5,460,182 a continuation-in-part of commonly assigned U.S. patent application Ser. No. 08/437,327, filed May 9, 1995 in the names of Daniel S. Goldberger and Robert S. Smith and entitled SURGICAL TOOL END EFFECTOR, and a continuation-in-part of U.S. patent application Ser. No. 08/024,278 filed Feb. 26, 1993 in the name of David A. Benaron and entitled DEVICE AND METHOD FOR DETECTION, LOCALIZATION, AND CHARACTERIZATION OF INHOMOGENEITIES IN TURBID MEDIA, which applications are copending and expressly incorporated herein by reference in their entireties.

FIELD OF THE INVENTION

This invention relates to surgical tools having a capability to image tissue and the structural and/or chemical composition of tissue over time during a dynamic surgical intervention, more particularly to tools that automate or provide better control over the surgical intervention, such as tissue welding.

BACKGROUND OF THE INVENTION

The opening of the body, in order to gain access to body parts, has long been a part of the surgical world. This began to change in the mid-1980's when some surgery began to be performed by introducing the concept that a video camera could be coupled to an endoscope, a hollow metal tube that goes into a body cavity through a small (usually ½ inch or less) incision or hole (also called a portal) in the skin, in order to perform major surgery through such a very small opening with a high degree of skill. This change has allowed many formerly "open" procedures, such as gall bladder surgery in which a long slit used to be routinely made in the abdominal wall to gain access, to be performed without opening up the patient at all. Such surgery, often termed minimally-invasive surgery, has revolutionized the way some surgeries are performed. Patients that benefit from this approach are now recovering much more quickly and comfortably than before.

As the emphasis on less invasive surgery has developed, surgeons are seeking less invasive ways to perform many common surgical interventions, such as sewing tissue together or killing a tumor. However, although techniques for surgical intervention, such as endoscopy, laser welding, cryosurgery, and others have advanced greatly over the past 20 years, the tools that surgeons are using on the patients often have not evolved substantially. For example, the surgical knife, suture, staples and clips have not changed significantly since their introduction.

Optical and other sensors for monitoring the external body are known. For example, Jobsis U.S. Pat. No. 4,380,240 refers to an optical system for monitoring the brain. This system is meant for external use only. More sophisticated externally dedicated monitors have been proposed by Hirao U.S. Pat. No. 5,057,695 and Giannini et al. U.S. Pat. No. 5,088,493.

Limited sensors have also been placed into some surgical tools. For example, Kubota U.S. Pat. Nos. 4,299,230 and 4,356,826 refer to pressure-sensor devices attached to surgical tools for the detection of the local pressure at the tip of a stabbing tool. Others have used an optical approach based upon allowing light to pass through an optical window in the surgical tool to the surgeon's own eye, such as that referred to in Riek et al. U.S. Pat. No. 5,271,380. Such a device allows the user to peer down the barrel of the surgical tool and visualize where the tool is located. Each of these preceding approaches is passive in the sense that each simply measures a static feature of the environment of the tool. These tools yield no new information when left in place and undisturbed. In contrast, during an intervention such as tissue welding, as the present inventors have appreciated, what is needed is feedback as to changes over time (evolution) in the tissue that would allow modulation or control of the surgical intervention, even if such changes occur deep in the tissue and well out of the region near the tip of the surgical tool. The same could be said for the scalpel, which blindly cuts, such that feedback concerning the progress of the intervention would be useful.

Others have proposed to use optics with surgical tools. For example, Matsuo U.S. Pat. No. 4,269,192, Lorenz U.S. Pat. No. 4,410,020, and Liese U.S. Pat. No. 4,566,438 refer to putting optical fibers into a needle or syringe to report on the location of the tool or device as it is placed into the tissue. A problem with these devices is that they do not report on the status of a tissue and, further, are not feedback systems suitable for controlling an intervention.

Alfano U.S. Pat. No. 5,131,398, Shaw U.S. Pat. No. 4,416,285, and others refer to placing optics in needles or catheters for distinguishing cancer from noncancerous tissue, or analyzing the content: of fluids. More sophisticated approaches are referred to in Vari et al. international application WO92/17108 and Janes U.S. Pat. No. 5,280,7880, which analyze tissue in an existing state to determine whether a tissue is or is not metastatic cancer, or to diagnose an existing condition of the tissue. However, a problem with these devices is that none teaches the use of such devices for the monitoring of changes over time in tissue as a result of an intervention, and more particularly using the detected changes to control the intervention.

One area where this deficiency in known surgical tools can be clearly seen is in surgical techniques that alter tissue thermally. Biological tissues, living or dead, can be altered by thermal stresses, such as heating using electric current, lasers, or ultrasound. Such techniques are becoming more common in medicine, and represent major advances in their fields. Currently, however, there is no simple method allowing for the real time monitoring of chemical or histological changes that occur as a result of thermal or other forces. Thus, the surgeon has such modern thermal techniques available, but no method of monitoring their effectiveness.

The lack of good feedback on the one hand, and automated tool control on the other, can lead to complications during surgery. One example is the use of thermal energy to weld the ends of blood vessels together, which is now known. Anderson U.S. Pat. Nos. 5,290,278, and 5,300,065 refer to applying thermal energy to weld tissues. Unfortunately, most surgeons are left on their own to assess when the weld is done correctly, and when it may be either under- or over-heated. Dew U.S. Pat. Nos. 5,140,984, 5,002, 051, 4,854,320, refer to using thermal measurements to measure the temperature of the tissue, or a fixed shutter time that limits the welding energy regardless of the state of the tissue. These nonradiative approaches do not, however, measure the effectiveness of the weld, as the strength of the weld varies over time, with structural changes in the collagen substrate (tissue), and varies with the temperature, such that temperature alone is not a good predictor of weld strength. This limitation has reduced the effectiveness and acceptance of laser welding techniques in surgery. Potter U.S. Pat. No. 5,219,345, refers to monitoring the reflections in a single fiber laser delivery system to determine to condition of the tip of the fiber nearest the tissue being treated. In addition, additional fibers can be added to the system to monitor back reflected light from the tissue to measure fluorescence. A problem with the foregoing is none provide a tool or method of probing the tissue to assess changes that would correlate with welding progress and/or weld strength, or even to monitor other invasive procedures such as ultrasonic warming or surgical ablation to monitor the progress and/or quality of treatment.

Another surgical intervention example is the use of electrocautery to sear tissues in order to control bleeding, or in order to cut tissues. Electrical resistance methods are known that allow the resistance to current flow in the tissue to be monitored. This method fails to perform well because resistance is a factor of many effects, such as hydration of the tissue and presence of blood, and does not effectively predict whether the tissue is cauterized or not. Thus, use of resistance techniques, while commercially available, have not been widely accepted.

SUMMARY OF THE INVENTION

Accordingly, an object of the present invention is to provide a noninvasive or minimally-invasive apparatus and methods for detecting chemical or histological changes over time in a tissue. In particular, it is an object that results of thermal interventions, such as those involving heating or cooling of tissue, can be monitored or imaged during a surgical process.

Another object of the present invention is to provide a feedback to the intervention, such as a thermal surgical process, using an analysis of the changes that occur in such tissue during the intervention, to improve the probability of a desirable outcome. Such feedback could be auditory, visual, or occur in the form of an automated control or interlock that directly controls the thermal surgical process.

Another object of the present invention is the reduction in the human skill set needed to perform a surgical intervention, such as electrocautery, such that the procedure can be performed more safely, rapidly, and reliably by surgeons of all degrees of experience, and reduce dependence upon long-term experience.

Broadly, the present invention concerns methods and apparatus to detect the chemical and histological changes occurring in the tissue by combining a surgical tool with a monitoring device to detect for such tissue state changes. The present invention also concerns a device capable of detecting chemical and histological changes over time in tissue, in a noninvasive or minimally-invasive manner.

The present invention creates a class of "smart" surgical tools that allow specific surgical intervention processes to be completed more efficiently and more effectively. Thus, the smart tool combines the measurement function of the present invention with a more conventional (or unconventional) surgical interventional function, such that the smart tool can perform a surgical tissue intervention and directly monitor the results of that intervention. Examples of such smart tools include, without limitation, electrocautery tools coupled with a tissue analysis device that allow automated spot welding of tissue or vessels, and facilitate sutureless (and stapleless) surgery, such that the smart tools operate with intelligence in real time and with a decreased risk of complications over current tools.

Another aspect of the present invention is to provide a tissue analysis device to be used with a surgical tool to provide feedback to surgeons so that ongoing, dynamic surgical interventions, for example, thermal intervention such as tissue welding, can be monitored and/or imaged, and optionally so that the monitoring can be used to make the surgical technique somewhat or fully automated. As a result, the present invention renders the surgical intervention technique safer, more effective, cheaper, or some or all of the above.

A salient feature of the present invention is the incorporation of an observation that radiative energy can be made to penetrate an opaque media such as tissue during thermal stresses, and then can be detected upon reemergence from that tissue. Further, the detected energy can be analyzed to allow real-time monitoring of a thermally-induced process or other surgical intervention, in a nondestructive, minimally-invasive manner. The detected energy may be light or selected light wavelengths that has been coupled through tissue, absorbed and reemitted such as in the case of fluorescence, and further the emitted photons may be altered on or by the environment such as in the case of Raman effect scattering.

Advantageously, the smart surgical tools of the present invention are not limited to a tissue analysis device that monitors the opaque medium from the outside, i.e., an exterior (epidermal) surface. Rather, the smart tool may be placed in direct contact with the surface to be measured, e.g., an internal organ or bile duct, or even internally into the tissue, e.g., inside the urethra, to allow monitoring of changes to occur proximate to, or from within, the tissue itself. In other words, the tissue analysis device may be kept in the same general location when the tool performs the intervention and moves with the tool, and still images tissue in a non-destructive manner.

In addition, the smart tool may include more than one probe to irradiate the tissue and detect the emitted radiation. Multiple probes may be used simultaneously such that multiple sites can be treated or a single site can be more effectively monitored and hence treated. Such multiple probe monitoring also provides for improved feedback into the thermal intervention process to shape the time course, three-dimensional shape of the treated area, or the rate of the thermal process. Such a goal may rely upon simple monitoring of the tissue, or upon construction of an image of the tissue treatment area.

Preferably, the surgical tool also is adapted to perform an additional intervention to test the tissue, during or following the conventional intervention. For example, in the case of a smart electrocautery tool, the tool may be constructed to permit squeezing and releasing the tissue in order to test for the presence or absence of capillary refill. This permits ascertaining the success of the electrocautery intervention.

Another aspect of the present invention is directed towards an improved surgical tool for conducting a thermal surgical intervention of tissue. One such tool comprises, in addition to the tool performing the desired thermal intervention, an emitter of radiative energy of at least one frequency which is directed into the tissue to be subjected to the thermal intervention, a detector responsive to a portion of the emitted radiative energy that has traveled through at least a portion of said tissue to be subjected to the thermal intervention, wherein the detector has an output signal corresponding to the detected radiative energy, and a computer analyzer that receives the detector output signal and processes it to determine status of the tissue portion as a result of the applied thermal intervention, and an output indicator signal corresponding to the determined status of the tissue portion. The emitter may be a light source, such as, without: limitation, an ambient light source, an infrared light source, a laser beam, and a light emitting diode (or more than one light emitting diode). The emitter also may be a fluorophore, a radio emitter, a radio wave source, and a self-emitting source, e.g., ultrasonic and piezoelectric devices or light-generating chemical or biochemical compounds such as a luciferase. The detector may be a light detector, for example and without limitation, a photodiode, a photomultiplier tube, a charged coupled device (CCD) element, a CCD array, a phosphor screen or an optical intensifier. In practice, any detector capable of detecting the emitted radiation having passed through the desired tissue portion or having been emitted in response to the radiation illuminating the tissue may be used.

As will become clear in the various embodiments described hereinafter, there may be one or more emitters and there may be one or more detectors. The detectors are preferably configured to be sensitive to the detection of radiative energy reaching the detector by a route that is selected from one or more of transmission, reflection, scattering, fluorescence, and remission of energy emitted into the tissue.

The computer analyzer preferably processes the output signal of the detector with reference to a preselected criterion or a set of criteria (hereinafter "preselected criteria") corresponding to a desired characteristic(s) of the tissue subject to the surgical thermal intervention.

In this regard, analysis of the detector output (or outputs when more than one detector is used) over time, is compared to the preselected criteria. A decision is made based on one or more of the following known processing techniques: class analysis, least squares fitting, chemometrics, and partial component regression. Of course, other techniques could be used.

Preselected criteria are preferably obtained by empirical study for the particular type of tissue being treated.

The emitted light detected at the detector is modified by the tissue as a function of one or more of the following characteristics of the tissue, as the tissue state exists at any point and time: absorbance, scattering, and anisotropy factor, elastic scattering, polarization, fluorescence, temperature, and thermal diffusion. It should be understood that the references in the specification and claims to a detector detecting radiative energy corresponding to radiative energy from an emitter passing through the tissue (and the various ways this description is written throughout the specification) should be specially construed to include, without limitation, direct radiative energy, that is the same radiative energy emitted by the emitter, as that radiative energy is modulated and/or attenuated by passage through the tissue, and indirect radiative energy, which occurs as a result of the emitted radiative energy passing through the tissue, as in the case of a fluorescent, luminescent chemiluminescent or electrochemiluminescent response to the emitted radiative energy and combinations of direct and indirect radiative energy, as the case may be. The precise number and configuration of the various detectors are believed to be a matter of design choice which is subject to cost constraints and balances based on, e.g., the processing speed and power of the computer analyzer and the ability to process multiple data inputs with sufficient accuracy and speed for the given intervention to obtain a meaningful result. For example, a time-of-flight analysis, which measures the time interval required for photons to traverse the tissue, is now known to be one method to separate out the effects of tissue chemistry (related grossly to absorbetnce of light) and tissue histology (related grossly to tissue cell histology). This can also be performed using frequency-domain techniques such as phase-shift spectroscopy.

Preferably, the output indicator signal is an alarm in that it indicates to the operator that a desired tissue status is about to be achieved, has been achieved, has been surpassed, or any combination of the foregoing. Preferably, the indicator signal may be used to operate a surgical tool in a manner that prevents the surgical tool from continuing the thermal intervention beyond a predetermined range of acceptable conditions, thereby preventing further change of the state of the tissue being operated on.

In a preferred embodiment, the tissue analyzer also is capable of generating an image of the tissue based on the detected radiation having passed through the tissue.

The surgical tool may be, for example, and without limitation, an electrocautery device, either uni-polar or bipolar, a hemostatic cutting or cauterizing instrument, and a laser beam, such as a laser knife.

Another aspect of the invention is directed to an improved surgical tool to assess changes in the status of surgical tissue during thermal interventions. One such tool includes:
  a light emitter for emitting electromagnetic radiation of at least one wavelength in the range of 0.2 micron to 10 microns into a first volume of tissue;
  a light detector for detecting at least a portion of said emitted light, said light portion having traveled through a second volume of said tissue, said second volume comprising at least a portion of said first volume;
  means for thermally altering the chemical and/or histological structure of a third volume of said tissue, the third volume comprising at least a portion of said second volume; and
  status measuring means for determining, based upon said detected portion of light, a status of at least one of said volumes of tissue related to said thermal alteration, said status changing as a direct result of said thermal alteration over time.

One such surgical tool is a bipolar electrocautery device to heat tissue. Another such surgical tool includes grasper means arranged to hold the tissue proximately coupled to the light emitter and light detector, and to maintain the tissue proximately coupled to the thermal means. The grasper means preferably includes a pressure control system for modulating the pressure exerted by the grasper on said tissue. Further, the pressure control system is controlled to provide compressive pressure over a range that is selected to provide one or more of the following: (i) an optimal tissue weld strength; (ii) optimal vessel ablation; and (iii) temporal pressure variation at a frequency and pressure range selected to assess the patency of blood flow in said tissue.

For a surgical tool having a thermal source that is a bipolar electrocautery device, the grasper means is preferably configured to grasp and seal tissue and vessels that are larger than 3 to 5 millimeters in diameter. The grasper means may be constructed with integrated fiber optics for emitting and detecting the light into and from the tissue, nonstick tissue contacting surfaces where appropriate, reusable materials, and mirrored light collecting or integrating features for detecting emitted light.

The foregoing aspects of the improved surgical tool may be further improved by providing feedback based on the determined status for modulating the thermal process in accordance with said determined status.

Another aspect of the invention is directed to a method of monitoring the status of tissue during a surgical intervention. One such method comprises the steps of:

a) emitting radiative energy of at least one wavelength into the tissue;

b) detecting at least a portion of the emitted energy, said detected portion having traveled through at least a portion of the tissue;

c) altering the chemical and/or histological structure of the tissue as a result of a surgical intervention; and, d) determining a change in a status of the tissue that occurs as a direct result of the surgical intervention, said determination being based upon the detected portion of the emitted energy.

Preferably, the step of altering the structure of said tissue includes the step of thermally altering a region of the tissue. The thermally altering step preferably includes applying an electrocautery heat source, more preferably a bipolar electrocautery source.

Preferably, the method step of determining a change in status includes the step of taking repeated measures of the detected radiation over time. The measures include the step of collecting and averaging repeated measures over time, wherein the said repeated measures are selected so as to provide improved accuracy and noise rejection, or to provide a measure of change in state over time, or both. Preferably, baseline measurements obtained from untreated tissue are obtained prior to the thermal intervention. Optionally, a reference measurement related to a predetermined tissue status (e.g., a target status) also is used in the analysis.

In another embodiment, the method step of taking repeated measures includes the step of collecting repeated measures over space. This permits generating an image of the tissue portion being treated in two or three dimensions.

Another aspect of the present invention is directed to an improved tissue monitor to assess the status of tissue during a surgical intervention. One such monitor comprises:

a) an emitter of radiative energy of at least one wavelength arranged to emit said energy into the tissue being monitored;

b) a detector proximately coupled to said tissue to detect a portion of said emitted radiation after having traveled through at least a portion of said tissue;

c) a status analyzer to determine an effect upon said tissue occurring as a direct result of a surgical intervention, said determined status being based upon said detected portion of radiation; and d) an output device having a signal corresponding to said determined status.

In this monitor, the detector is arranged to be, for example, in touching contact with the tissue, invasively placed into the body but not necessarily in contact with the tissue, or invasively placed into such tissue.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIGS. 7A, 7B and 7C illustrate a multiple emitter and multiple detector arrangement for a variation of the smart tool of FIG. 6A and representative test results;

DETAILED DESCRIPTION OF THE INVENTION

The apparatus and methods of the present invention are better understood by reference to the following examples. These examples are by no means intended to be inclusive of all implementations, uses, and applications of the present invention. Rather, they merely serve as indicators of some uses by which a person, skilled in the art, can better appreciate the methods of utilizing, and the power of, the devices and methods of the present invention.

EXAMPLE 1

Optical Monitoring of Tissue Heating

The detection of spectroscopic changes that occur during heating of tissue are important in tissue welding and sutureless surgery, as well as in other situations such as the ultrasonic heating of tissue in order to kill a tumor. In these processes, it is important to detect the degree of chemical and histological change within the tissue, and in particular to detect when the proper stage of thermal change has been reached. This detection is important to minimize risk of collateral damage or incomplete treatment, and to maximize success, such as optimum weld strength and integrity in tissue welding, or optimum tumor killing in cancer treatment.

Chemical detection of tissue denaturation during heating caused by electrocautery current has been demonstrated in accordance with the present invention in laboratory experiments. The test was designed to determine whether or not spectroscopic changes occur in tissue as heating occurs, and whether such changes could be used to identify various stages of tissue doneness. It is believed that the results based on heating caused by electrosurgical tools are applicable to other heating instruments, such as thermally regulated or autoregulating devices; that transfer heat by conduction, convection, induction, or radiation.

Figure 1:
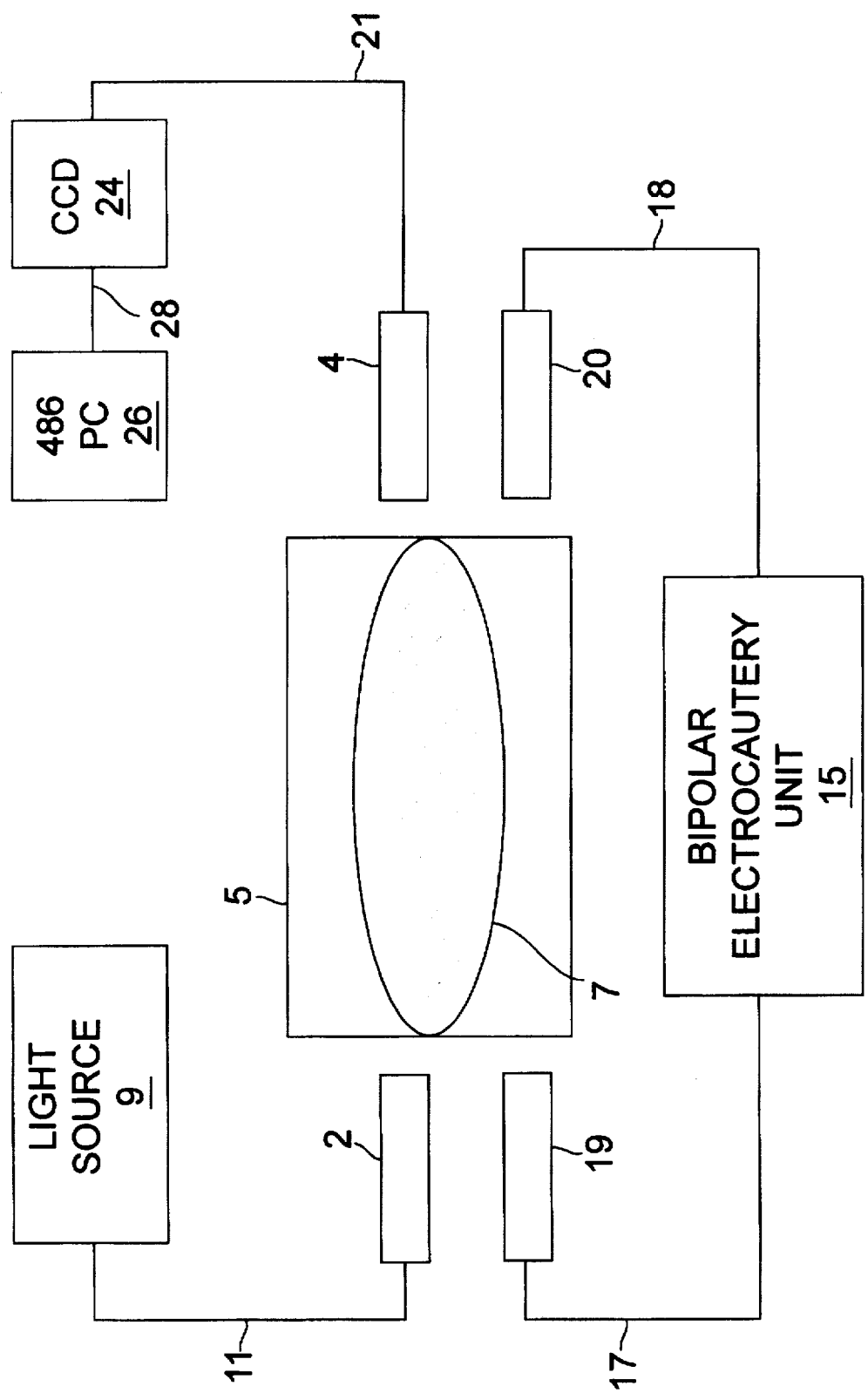
FIG. 1 illustrates a schematic block diagram of a smart tool apparatus in accordance with an embodiment of the present invention.

With reference to FIG. 1, the apparatus representative of a smart surgical tool in accordance with the present invention included an electrocautery function and a tissue state monitoring function. The latter included a light emitter 2 and detector 4 placed upon opposite surfaces of the tissue to be subject to the intervention, in this embodiment a plastic cube 5. Cube 5 contained a sample tissue 7. A light source 9, preferably a broadband light source such as a Xenon arc lamp or krypton-filled filament bulb, was coupled to emitter 2 by an optical fiber guide 11. Tissue 7 was made of chicken breast meat and chicken fat strips. A commercial bipolar electrocautery unit 15, e.g., model Force 4B available from Valleylabs, was used to pass current through electrical wires 17 and 18 connected to electrical contacts 19 and 20 disposed on opposite sides of tissue sample 7, respectively. Spectroscopic data from emitter 2 and detector 4 was collected by a CCD spectrophotometer 24, in this case Ocean Optics model SD-1000, and the collected data was provided over cable 28 to a computer 26, in this case a Intel model 80486-DX50-microprocessor based system. Computer 26 recorded spectra from tissue 7 at discrete wavelengths ranging between 400 nm and 1100 nm in 1024 channels, with one spectrum recorded every 25 ms.

Figure 2:
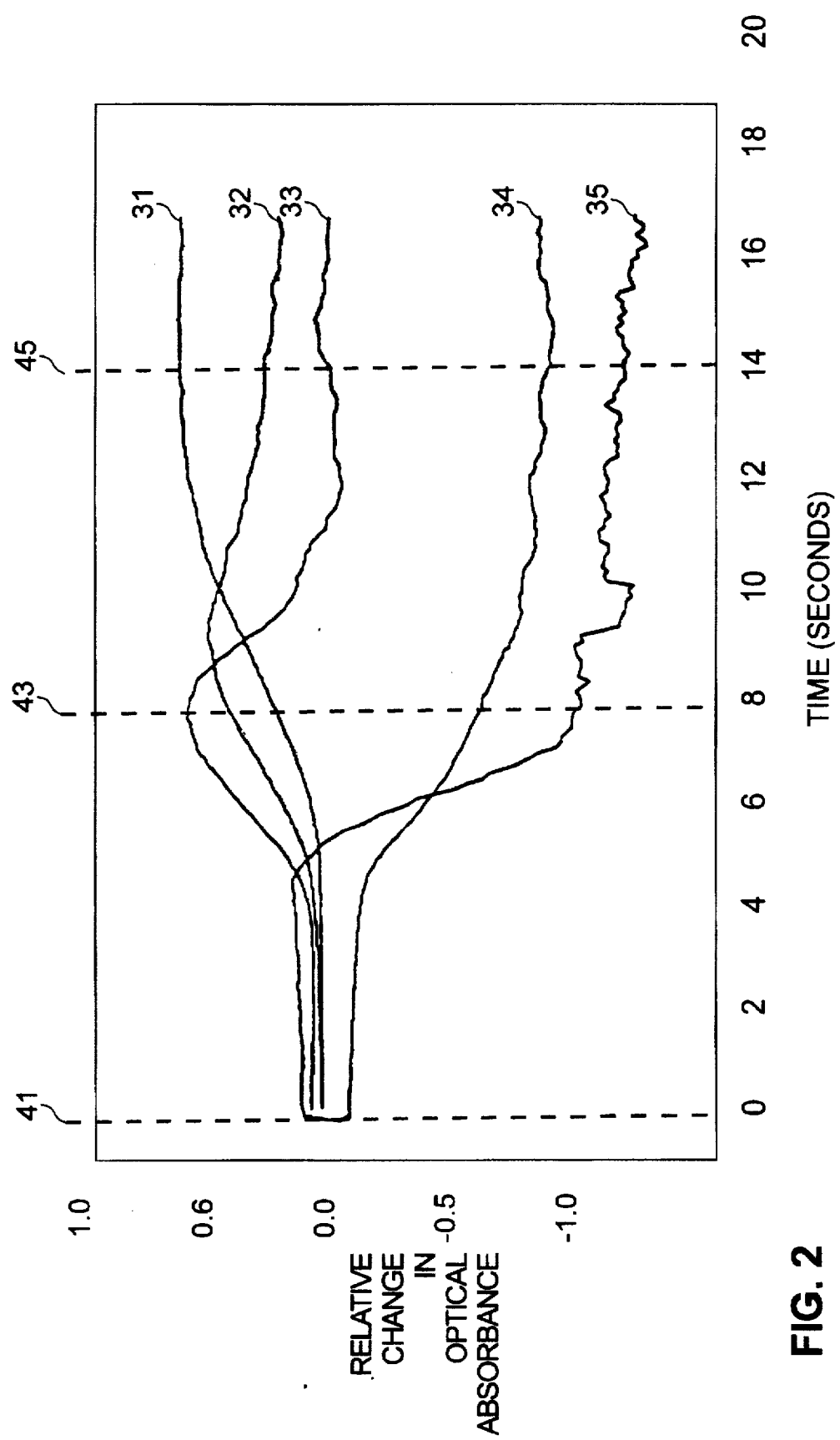
FIG. 2 illustrates a determined relative change in optical absorbance over time for different wavelengths in tissue subject to electrocautery in vitro.

The results of this experiment are shown in part in FIG. 2, as a series of transmittance curves at different wavelengths (absorbance is inversely related to the transmittance). Most of the spectra have been eliminated for clarity. Transmittance curve 31 was collected at 629 nm, curve 32 collected at 576 nm, curve 33 at 559 nm, curve 34 at 891 nm, and curve 35 at 468 nm. At the start of current flow through tissue 7, the transmittance spectra are essentially stable, for example, at time point 41. As tissue 7 is heated it becomes more opaque, proteins coagulate and denature, and there are significant, notable transmittance changes in all curves. These changes represent both histological changes and chemical changes in the tissue. However, not all changes occur uniformly. For example, both curves 34 and 35 decrease over time. The extent of changes differ, with curve 35 showing a relatively greater change in transmittance. Curve 31 shows an increase in transmittance over time. Curve 32 shows the appearance and disappearance of transmittance over time, suggesting that there is a chemical process going on that may yield clues as to the extent of denaturation. Similarly, curve 33 shows the appearance and disappearance over a different time course.

Thus, as tissue was heated, the spectrographic signature of tissue 7 changed. These changes allow an assessment of the progress of the heating process, including the loss of water as the tissue became heated to the boiling point. The nonuniform spectroscopic changes thus offer indicators to the changes that are occurring in the tissue, which changes are believed due to the change in various compounds and their frequency selectively as those compounds undergo chemical and/or histological changes with temperature. Thus, by empirically establishing spectroscopic signatures for desired tissue state, the test apparatus serves as the basis of a probe for the determination of whether tissue has been denatured to the correct point in the desired electrocautery intervention. Such data can be processed in multiple ways. For example, a class analysis can be performed (Haaland, 1989) that would allow use of such data to generate a model for determining which selected spectra fall into each of the tissue type to be treated at the native or underheated tissue, welded or properly heated tissue, and overheated tissue groupings. Or, the spectrum of the ideal level of electrocautery (e.g., empirically determined) could be stored in memory, and a least-squares fit performed until the spectra of the tissue under treatment begin diverging rather than converging, such that that point is identified as the point of ideal tissue heating cooking. Alternatively, a partial components regression can be performed (Haaland, 1989) that would allow assignment of a "doneness" score, with a median score representing tissue perfectly heated, a low score representing native tissue, and a high score representing tissue that has been over-cauterized.

The exact mathematical model used is not important, provided only that a series of spectral characteristics can be identified that allow automated calibration of the identification method. Such methods may use the collection of a reference spectrum from the tissue, such as over a normal area of tissue, to serve as a basis for the measured changes, or may include multiple measures over time in order to either average the spectra, and thus decrease the noise, or to measure changes and rates of change in order to better guide the intervention. It is also possible that multiple detectors and multiple emitters may be desirable, such that the determination could be performed in multiple dimensions or as an image, as described elsewhere herein.

Advantageously, the present invention provides a smart surgical tool that can perform a tissue heating function, electrocautery, thermally regulated heating devices and laser based heating devices, and monitor the progress of the thermal reaction to identify or indicate when the desired thermal affect has been obtained.

Other applications of the smart surgical tool of the present invention can be envisioned. Such a probe could be used to tell if a consumer's hamburger or steak is properly cooked, possibly replacing the thermometer, which simply measures temperature of the meat, and not the state of denaturation. For example, spectroscopic device could tell you exactly when the meat is rare, medium rare, or well done.

EXAMPLE 2

Tissue Welding

The apparatus of example 1 also can be applied to living tissue in an operating room environment. In certain types of cancer, treatment is achieved by heating the tumor using ultrasound, radiation or electricity, allowing killing of the tumor without having to cut up tissue in order to remove it. Heating can also be used to perform tissue cutting, ablation of blood vessels to stop or prevent bleeding, and more recently has been used to replace the function of sutures (and staples) during surgery. It is toward the last category that this second example is particularly directed.

Surgery is most effective when it is done rapidly and with minimum blood loss. Surgery underwent a major boost in the 1980's when suturing, the method of applying surgical ties to tissue, was in part replaced by rapidly applied clips and staples. These tools made surgery faster, and the patient (as well as the surgical team and hospital) received the benefit.

A newer method of performing surgery concerns replacing the tasks for which sutures or clips are needed with electrocautery welding. In short, the concept is to use the thermal power of the electrocautery tool to weld tissue together. Much the same phenomenon occurs when a hamburger is cooked on a grill, and the proteins sear the meat to the grill in quite an effective manner. This same effect can be used to close off blood vessels, allowing large sections of tissue to be removed without the need for clips, staples, or sutures.

The problem limiting application of this new surgical approach is that, unlike a knife which damages only the tissue it touches, a laser, thermally heated device or electrosurgical knife can damage nearby tissues by killing, or even destroying (charring), depending upon the current or thermal energy applied and the time the tool is used. Often, distinguishing between the states of killing, searing, or cutting can be quite difficult in practice. For example, when preparing a tissue for surgical removal, it is necessary to shut off blood supply to the tissue. This is traditionally done with sutures, though suturing is time-consuming, can rupture tissues and cause bleeding itself, and can be a focus of infection. Thus, alternative methods of closing blood vessels are being sought, such as electrocautery and thermally heated hemostatic devices. If done properly, using the right time, current, and pressure, larger vessels can be seared together, preventing bleeding during tissue removal. Further, such a sealed site will heal correctly because the tissue that is left will form a strong scar. This approach can also be used to tack down tissue using spot-welds, and even to reseal open compartments, such as blood vessels.

In accordance with the present invention an approach and tool using electrocautery have been developed to sear and close off larger vessel areas, to tack down large tissue cross-sections, and even to seal open blood vessels, that overcomes the problems heretofore associated with the technique. Too little current, and the tissue bleeds profusely when cut; too much current will char the tissue, and charred tissue will fall apart, posing a risk of bleeding several days later and/or improper healing. A good cut will "brown" the tissue, or even simply "blanch" the tissue, and does not bleed as the blood is coagulated and capillary bed destroyed.

Figure 3:
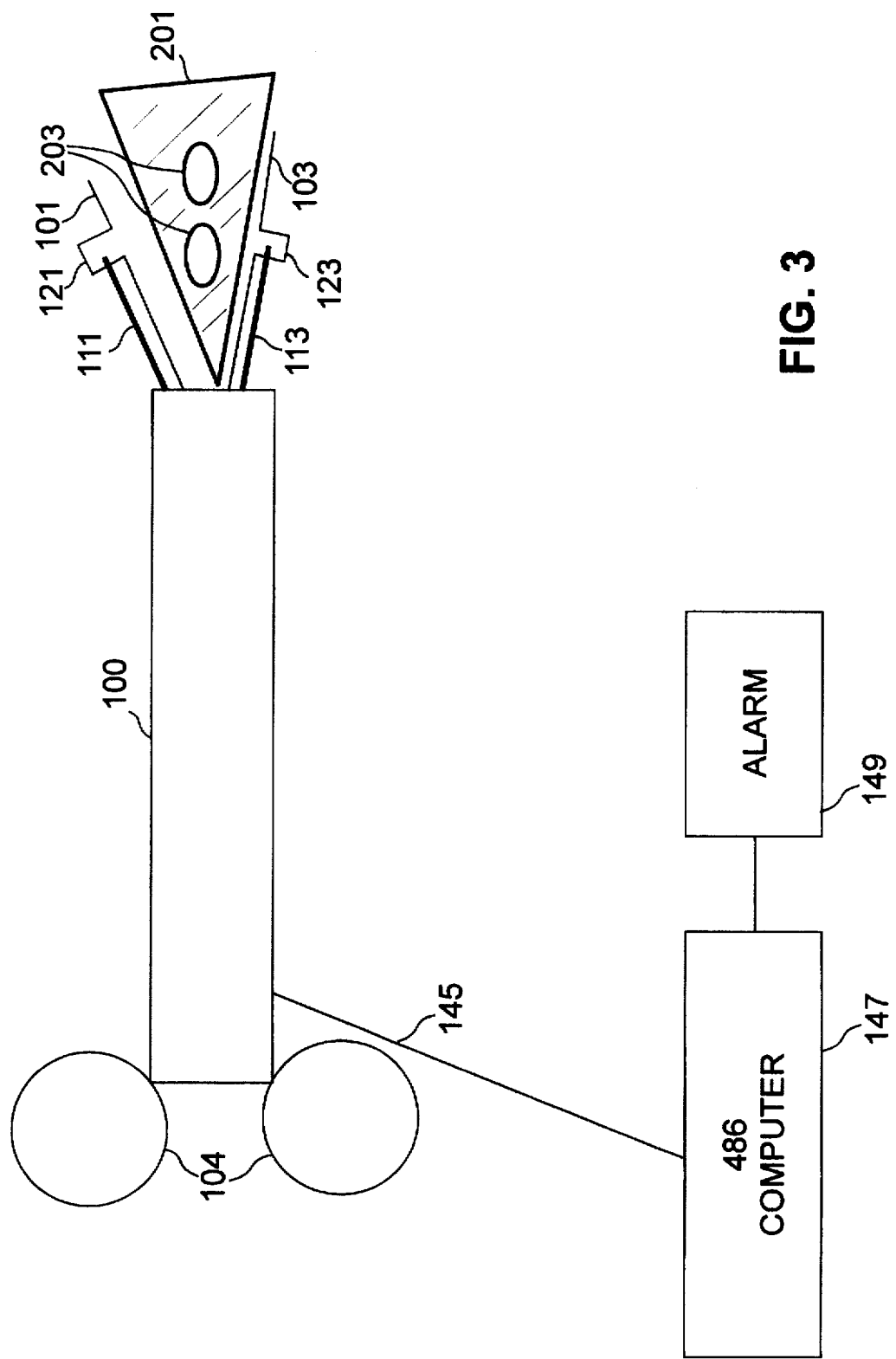
FIG. 3 illustrates a schematic diagram of an embodiment of smart surgical tool in accordance with the present invention.

It requires much skill and experience for a surgeon to make the proper assessment between too little, too much, and just the right amount of electric current by the look and feel of the tissue. Accordingly, the present invention provides a semi- or fully-automated electrocautery tool system to determine tissue doneness based on spectroscopic analysis, for assessment and control of progress during an electrocautery intervention. With reference to FIG. 3, an embodiment of such a tool 100 is shown. In tool 100, the current passes between a pair of grasper members 101 and 103 which also form a pair of electrocautery jaw members, and which are opposed jaws mounted on shaft 104. Jaws 101 and 103 pass current to heat tissue interposed between said jaws. Optical fibers 111 and 113 are disposed to terminate in mirrored wells 121 and 123 located in metal jaws 101 and 103, and collect light in the wells. Optical elements (not shown) may be inserted in wells 121 and/or 123 to enhance coupling light between the tissue and the optical fibers. Fibers 111 and 113 are connected via cable 145 to optical signal processor 147, that sounds an alarm 149 to alert the surgeon that the process has been sufficiently completed. Optical processor 147 includes a computer such as that described in connection with Example 1, having additional functionality for generating alarms when one or more predetermined criteria are met (or exceeded). Optionally processor 147 also controls the delivery of electrocautery current through grasper members 101 and 103 in response to the status of the tissue. In an alternate configuration, the light emitting element may be located within a mirrored well, such that the light source is coupled by a wire to a controller that is a part of processor 147. Such a light emitting element may be a krypton-filled filament bulb, or one or more light emitting diodes (LED), for example.

Figure 4A:
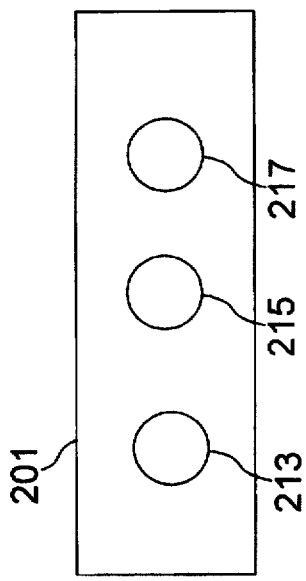
FIGS. 4A–C illustrate the ablation state of three blood vessels using a smart electrocautery tool in accordance with the present invention.
Figure 4B:
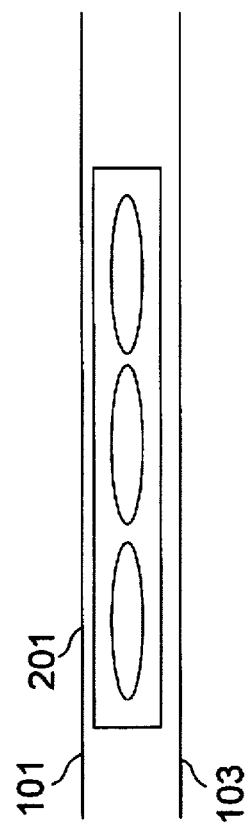
Figure 4C:
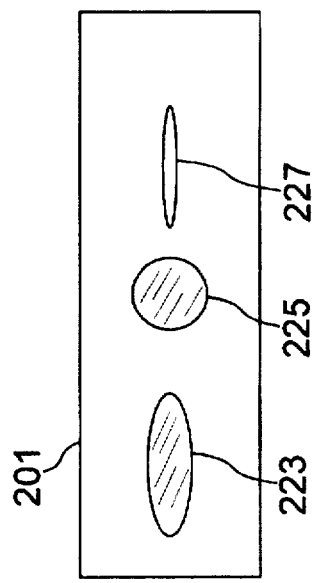

FIG. 4 illustrates how tool 100 could be used to occlude blood vessels with appropriate spectroscopic analysis of the state of the tissue under treatment to determine the time when the intervention procedure is complete. As a result, the invention allows subsequent cutting of such occluded vessels without the need for suture, clips, or the like. In FIG. 4A, tissue 201 is shown having three vessels, arteries or veins, as vessel 213, vessel 215, and vessel 217, before pressure and thermal treatment. In FIG. 4B, electrocautery jaws 101 and 103 are shown compressing tissue 201, with the blood vessels compressed. In FIG. 4C, the tissue is shown after treatment by several methods of vessel occlusion. Vessel 213 is somewhat compressed, and is occluded with blood and coagulated, protein, shown as occluded vessel 223. Vessel 215 is not compressed, but is occluded with coagulated blood and proteins, as occluded vessel 225. Vessel 217 is shown welded into a compressed and occluded form, as welded vessel 227.

The present invention provides both advantageous and surprising results. First, most surgeons use unipolar instruments that direct current from the tip of the electric knife through the body to a grounding plate electrode, commonly placed under the patient. When they use such a device, large amounts of current pass through tissue that is not meant to be cut or seared, and thus searing small or large areas risks collateral damage. An advantageous technique for tissue welding or searing, known as bipolar electrocautery, can be used that instead directs current between two tongs (or relatively closely positioned electrodes) of the device, e.g., as shown in FIG. 3, thus sparing nearby tissue that is not directly or nearly-directly between the electrocautery jaws 101 and 103 from electric current. However, most surgeons do not use such a device and are not familiar with the potential use as a tool for controlling injury. Second, most surgeons are trained that one should not use electrocautery on large vessels, such as arteries larger than 5 mm in diameter and veins larger than 3 mm in diameter (arteries are easier to close off as their thick muscular wall sears nicely, but veins are harder as they have thin walls that do not close off so easily). Thus, the surgeons who utilize electrocautery, even bipolar electrocautery, are actually taught away from using electrocautery to perform procedures such as tissue welding. Third, most surgeons estimate whether tissue is "cooked vs. burned" by eye, even though such estimates may not be reliable. Further, most surgeons find the welding properties of electrocautery to be unpredictable, particularly if used in larger tissues areas and larger blood vessels. Even those who are skilled in the art of electrocautery welding techniques may still find it difficult to control tissue welding. Thus, the skill barrier that must be crossed in order to perform this technique is effectively prohibitively high. This is particularly important during minimally-invasive surgery performed using an endoscope-type instrument (e.g., surgery performed through a periscope-like tube without opening up the patient). If a portion of tissue, such as an artery, is improperly or not fully coagulated, this tissue will bleed profusely when cut, and may force emergency surgery (due to the blood loss and its attendant risks, as well as the fact that blood will block the endoscopic field of view, preventing further surgery via the endoscope in some cases). At the very least, such bleeding leads to worsening of scarring, and lengthening of surgery; at the worst, such bleeding can be a life-threatening complication of surgery and, hence, a cause of permanent injury or even death.

The present invention advantageously overcomes these problems by automatically monitoring the tissue state and determining how cooked or coagulated tissue has become, in real time, as electric current is passed through a set of bipolar tong electrodes.

The device illustrated in FIG. 3 has been tested, in living piglets. During the tissue denaturation process, as current passed through the tissue between a pair of tong electrodes 101 and 103, the appearance and disappearance of several different compounds, including the loss of water as the tissue became desiccated from overheating, was noted, much in the same manner as shown in FIG. 2. By incorporating such an information profile into an automated system, by means of feedback control, the tool generates alarms to warn the surgeon of changes in the state of tissue, and optionally, automatically shut down (i.e., stop the flow of current) or modulate the current when tissue is correctly cauterized, instead of burning tissue or causing other types of injury. Such alarms can be visual, e.g., indicator lights (not shown) on the shaft 104 of tool 100 indicating by color or location the relative state of tissue being monitored, a visual display in the endoscope view, audible alarms, for example, providing an increasing frequency or duty cycle indicating the state of the tissue or some combination thereof, of course, a manual override can be provided in the case of an automatic shut down. The current modulation is used to control the energy delivery to avoid tissue damage by, for example, selection of an appropriate duty cycle. Modulation can facilitate treating tissue adjacent to the just treated tissue by appropriately changing the duty cycle to the appropriate state and re-treating that tissue.

The specific triggering event used by a smart surgical tool in accordance with the invention could vary, but could include such measures as the disappearance of spectral signal corresponding to the presence of blood, or a class-analysis approach that searches for a color signature associated with properly browned tissue, or both. Similarly, char has a spectral signature that is different than tissue, whether based upon absorbance or scattering, or both, which can be used as a boundary for the safe operating condition. For example, a bipolar knife tool in accordance with the invention could shut down when an artery is fully baked, and there is minimal danger of bleeding if the tissue is subsequently cut. This would prevent overcooking, which can cause bleeding well after surgery due to improper healing, as well as undercooking, which will lead to immediate bleeding when the tissue is cut by the surgeon. The optical monitoring is preferably performed using optical fibers structurally integrated within the surgical tool. Alternatively, the optimal monitoring function could include a hand-held probe device that the surgeon places on or near the tissue to be monitored or a separate probe tool that is guided to be positioned proximate to the tissue to be operated on, e.g., through the same or a different portal in the patient. In any case, the result is safer, more effective surgery.

The proposal for sutureless surgery described herein has, in fact, now been performed on actual patients, with good results, as reported in the literature, e.g., see Nezhat et al. "Laparoscopic Radical Hysterectomy With Paraaortic and Pelvic Node Dissection".*Am J. Obstet. Gynecol.* 1992; 166: pp. 864–5; Nezhat et al., "Salpingectomy Via Laparoscopy: A New Surgical Approach".*Journal of Laparoendoscopic Surgery*, Vol. 1, No. 2, (1991), pp. 91–95; Nezhat et al. "Operative Lapersocopy (Minimally Invasive Surgery): State of the Art," *Journal of Gynecologic Surgery*, Volume 8, No. 3, (1992) pp. 111–141. In particular, for example, several hysterectomy operations have been performed without sutures, except at the skin, using the cauterizing principles outlined above. The results of such welding in vivo are now being studied by pathologists, and the exact mechanism of this welding is expected to become understood better over time. It is currently believed that such welding ablates the central cavity of the fused vessel. These patients have nearly all done well, and have had a lower complication rate with respect to bleeding than patients treated in the conventional manner with sutures or staples. Further, their surgeries were performed more rapidly, with less time needed for recovery, and at a lower overall cost than conventional surgery.

The advantageous combination of the tissue state sensing hardware and procedures for monitoring tissue and with feedback controlling the application of basic surgical tools, represents a fundamental turning point in the manner by which surgery may be performed.

Although the above examples have described electrocautery, the methods of analysis can apply to any method of heating tissue, such as lasers, lasers and "solder" dyes, hot probes, hemostatic cutting and coagulating instruments, ultrasound, diathermy, radiation treatment or other radiative energy approaches. Similarly, other influences upon tissue, such as ultrasound could be followed spectroscopically. Also, use of fluorescent emissions during heating may provide valuable information regarding the tissue state, particularly for any fluorescent wavelengths that appear or disappear as a particular tissue state is reached, or in changes in the fluorescent relaxation times with temperature. Also, time resolved methods, known to those skilled in the art of tissue optics, can be used, such as those discussed in Benaron, *Science*, 259:146:3–6 (1993), which is incorporated in full into this specification by reference. Frequency-resolved and multi-detector spatial methods can perform similar separation or absorbency and scattering, in addition to image the monitored tissue, and deemed to be within the scope of this invention.

EXAMPLE 3

Loss of Pulsatility as Tissue is Denatured

Two conditions must be satisfied for tissue to bleed: First, there must be a hole in a blood vessel, and second, there must be blood flow. The tissue welding takes responsibility for closing the hole. On the other hand, spectroscopic or optical methods could be used to detect either the loss of a signal related to the presence of hemoglobin (e.g., the blood has been destroyed in the vessel) or that the flow has stopped. Tissue in which arterial blood is flowing demonstrates a well-known pulsatility of signal. As tissue is thermally coagulated by a bipolar device or even a unipolar probe exerting pressure on the tissue, this signal disappears. Next, as the pressure of the device is removed, the venous blood will flow back into the tissue.

In accordance with the present invention, a spectroscopic method is used to detect the flow of blood back into the tissue, demonstrating the patency of the venous system. Thus, spectroscopy can be used to verify if the blood flow has been adequately destroyed.

Figure 5:
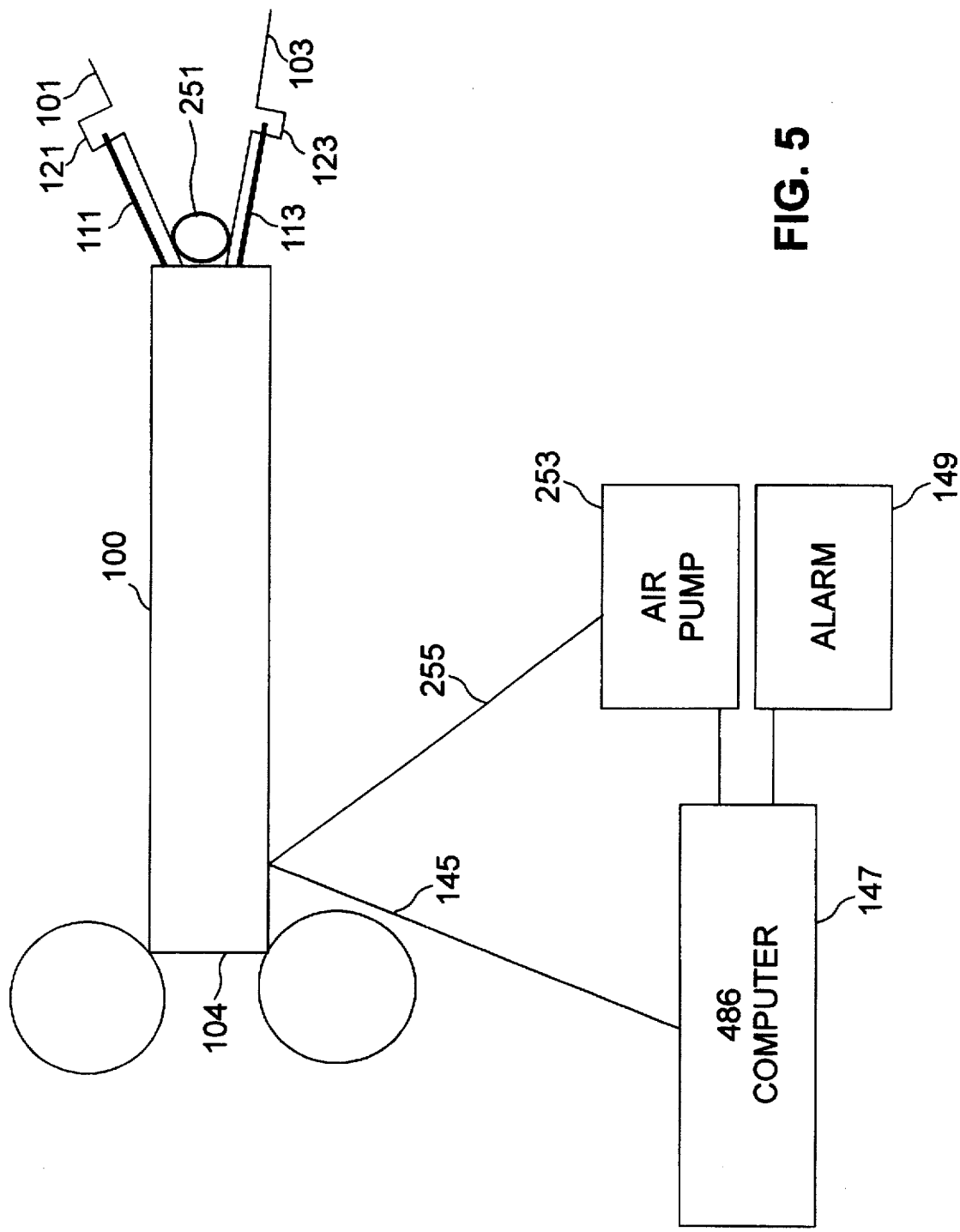
FIG. 5 illustrates a schematic diagram of a smart surgical tool having an air bladder to modulate pressure placed on tissue in accordance with an embodiment of the present invention.

One manner of implementing such a system is to provide a tool having optical fibers disposed in the probe to monitor the tissue proximate to the probe. The presence of pulsatility and/or capillary refill when pressure exerted by the tool is removed could allow identification of the point at which blood flow no longer occurs in the tissue. In this regard, with reference to FIG. 5, the tool 100 is modified by having a pneumatic system such as an air bladder 251 to open and close controllably grasper jaws 101 and 103, or to close the jaws and then release some pressure and then reapply pressure, allowing blood to refill the tissue at times. This change can detected by the spectrophotometer, and the absence of change as the pressure is modulated can be used to determine the time at which occlusion has occurred, and an alarm needs to sound. The opening and closing effect can be achieved by having air bladder 251 inflated by a pump 253 and hose 255 under operative control of processor 147. The movement of the jaws 101 and 103 also may be effected by mechanical or electromechanical devices, e.g., a manually operated cable, or a cammed motor cable connection. Other, non-optical tissue monitoring methods and devices could be used to determine the loss of flow, such as, for example, doppler ultrasound, to test for pulsatile flow.

EXAMPLE 4

Vessel Welding

Surgeons are now using lasers to weld together the ends of blood vessels previously severed in two, rather than suturing them together. This use of laser is difficult to control, and much effort has been directed toward control using temperature. The present invention however, provides the use of spectroscopic tools to monitor the state of the tissue as the laser welding process progresses as a key element in such control.

In this hypothetical example, the tissue being welded, namely the vessel sides are monitored using optical monitor disposed at the welding site. The laser, e.g., a $CO_2$ laser or other laser capable of heating tissue as are known in medical applications, is then controlled in the welding process to heat the tissue to the desired state for welding. In this case, the laser is automatically turned off or the heating intensity is reduced, when the monitored tissue state corresponds to a good weld. Thus, the correct strength is reached on each weld. As a result, a sequence of overlapped spot welds and a continuous laser scanning technique can be used with the spectroscopic monitoring of the present invention.

In one embodiment, a second laser that does not alter the state of the tissue, e.g., a helium-neon (red) laser, is used for indicating the heating spot. The optical monitoring system, namely the optical fibers, can then be disposed on a probe placed at this heating spot, either in the plane of the weld joining the several tissue ends together or perpendicular to that plane.

In this regard, a plurality of emitters and a plurality of detectors may be used, such that each emitter is paired with a detector to acquire information regarding the status of the tissue over space (i.e., an area of tissue). On the one hand, the space may be a line, for example, a plurality of emitter-detector pairs spaced along a tissue seam to be welded closed. In this regard, the emitters E could alternate position with detectors D, in a paired EDEDED relationship, or a single emitter could be used with multiple detectors, e.g., DDEDD, or the emitters located on one side of the seam and the detectors located the other side, or some other useful combination. In this embodiment, a useful construction of the emitter-detector structure for imaging is as a probe separate from the surgical tool performing the intervention. This permits leaving the probe in place and moving the tool in the area being monitored to better control the intervention.

In another implementation, multiple emitter-detector pairs could be arranged at angles to one another, and with the same or different spacing between each emitter and detector so as to permit construction of an image in two or three dimensions. The use of more pairs may require a more powerful data processor (and related decision algorithms) but also will likely provide more accurate information regarding, e.g., the success of the intervention, the patency of blood flow and the quality of welded (or coagulated) tissue. All or selected ones of combinations of emitters and detectors could be measured, and emitters and detectors could be provided at right angles or other angles to those shown, in order to generate good coverage of the tissue. Analysis of the data could then be used to generate data representing the distribution of tissue status and this data could be used to form an image. Such an image could be formed by techniques reported by Benaron et al., "Optical Time-of-Flight and Absorbance Imaging of Biological Media", *Science* 259:1463–6 (1993), and Benaron et al., "Tomographic Time-of-Flight Optical Imaging Scanner with Non-Parallel Ray Geometry", *Applied Optics* [In press] (1995), or by other methods, and the orientation of the emitters and detectors could vary in distribution and scanning patterns. In addition, spectroscopic analysis could yield improved images, without violating the spirit of the invention.

In addition, the light sources and detectors may be arranged to provide time-resolved light detection (e.g., as provided in the Benaron *Science* article for optical tomography), which is incorporated herein by reference, or by frequency-domain, or multi-detector spatial techniques, each of which would allow separation of scattering and absorbance, for example, using conventional methods known to those skilled in tissue optics.

EXAMPLE 5

Monitoring of Tissue Denaturation or Cooking

As discussed above, the use of monitoring of tissue denaturation can be important during surgery. In this example, it is shown how such data, using multiple emitters and detectors, can be turned into an image.

The effects of cooking in tissue using heat or electrocautery have been measured (other forms of tissue heating could be monitored equally well) and it has been shown that the distance light travels through cooked tissue is dramatically different than the distance light travels through normal tissue of the same type. There also are difference in the spectrum of the component parts of the tissue as cooking occurs, as noted in Example 1.

Light travels, on average, 3–5 times further through normal tissue than through air of a similar physical distance. As the absorbance of light is proportional to the distance traveled through tissue, increasing the distance light travels increases the apparent absorbance by four fold, due to the scattering of light by the tissue. As the tissue cooks, the distance traveled can be as much as 30 times or more as far through tissue as through air. Taking that ratio of absorbance versus the thickness of tissue through which the light travels should yield a constant for fully cooked tissue, and a different ratio for normal tissue. Thus, such a ratio can be used to discriminate cooked from normal tissue. In practice, the process of tissue denaturation is complicated, but for simplicity it shall be assumed that tissue exists in only two states: denatured (cooked) and normal. It is assumed that one skilled in the art, once shown a method for differentiating two states, would be capable of extending this technique to one in which there are multiple states of the tissue, such as ones corresponding to different states of denaturation, and that an image can similarly be formed for the complex case, and falls within the scope of this invention.

Figures 6A, 6B:
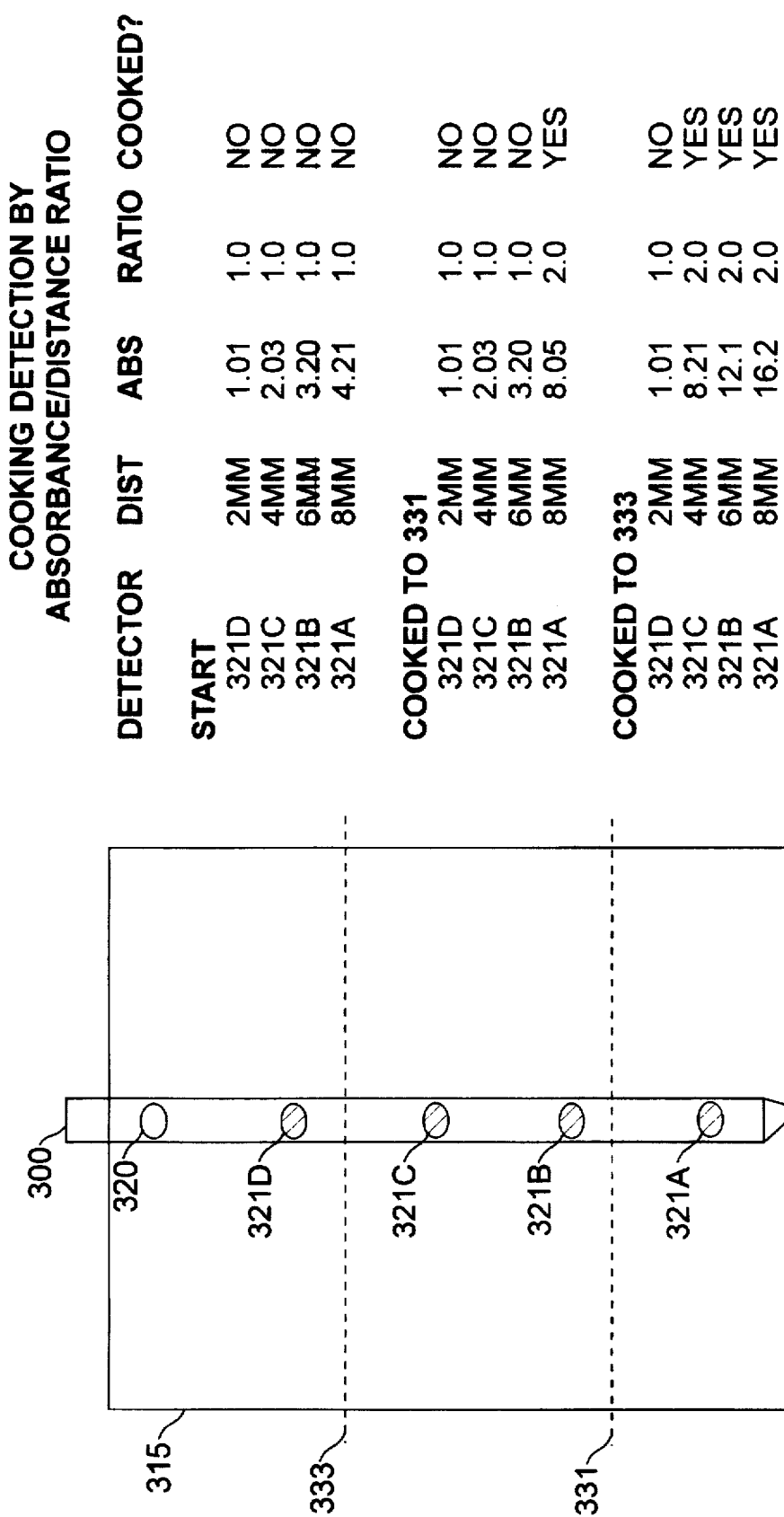
FIG. 6 illustrates a schematic diagram of a smart surgical tool for invasive thermal intervention and monitoring (FIG. 6A) in accordance with an embodiment of the present invention and representative test results (FIG. 6B)

One method of performing thermablation of tumors, for example, involves the insertion of a long probe into the tissue, and the tissue is cooked from the heated tip of the ablation instrument. Such a setup is shown in FIG. 6. In FIG. 6A, tool 300 with sharp, tissue penetrating end 305, is inserted into tissue 315. The tissue cooking occurs from heated tip 305 of instrument 300, inserted deeply into tissue 315. At the portion of the tool nearest the surface of insertion is light detector 320. Along the length of the probe are light emitters 321A, 321B, and so on through 321N. In this example, the emitters 321 and the detector 320 are placed with centers about 1 cm. apart.

Results from one experiment are shown in the table in FIG. 6B. The distance of each emitter from detector 320 is shown in the table in FIG. 6B as "dist." Initially, a baseline light level at detector 320 is recorded as each of emitters 321A–321N are sequentially illuminated. These values are recorded, and then changes from this baseline over time are recorded. Hypothetical absorbance values to demonstrate how cooking thresholds can be localized are shown in FIG. 6B as "abs." The ratio of current to original absorbance is shown as "ratio" in FIG. 6B. At the start of the experiment, there has been no effect of the heating probe on the tissue, and the relative absorbance at each emitter-detector fiber pair is near unity. This is shown in the section of 6B marked "Start." As cooking progresses, and the absorbance increases at the wavelength selected, the ratio increases. As cooking reaches line 331 in FIG. 6A, the cooking front has passed emitter 321A, and the light level passed to detector 320 has now changed. This is reflected in a high ratio. On the other hand, the light from the uncooked emitters has changed little. Thus, the cooking can be located as between emitter 321A (cooked "YES") while emitters 321B–D show no cooking (cooked "NO"). Once the cooking front has passed point 333, then emitters 321A–C are in cooked material, and have now been labeled cooked "YES." From such measures, the depth of cooking can be determined and displayed on a monitor as the cooking depth distance.

EXAMPLE 6

Imaging of Cooking

One problem in thermal ablation is that nearby tissue can be damaged by heat. The use of an alternating emitter/detector probe can allow a flexible imaging probe to be formed. This probe can be passed into tissue, and the proximity of the thermally cooked tissue to the probe can be imaged. Then, the surgeon can stop the cooking before it reaches the sensitive tissue.

Such a technique is described with reference to the tool 300 shown in FIG. 7. Tool 300 is now inserted into tissue 322. Emitters 323A, 323B, and so on through 323N alternate with detectors 324A, 324B, and so on through 324N. Denaturated tissue 325 resides in the tissue, not the site of the heating probe (not shown) but away from the imaging probe (tool 300 in this example), just to the left of emitter 323C. Using the amount of light transmitted between different pairs of emitters 323 and detectors 324, the depth of the cooking ball 325 can be assessed in a similar manner to that used to calculate depth of cooking in FIG. 6. Such an approach works as light penetrates deeper into the tissue as the emitter and detector spacing increases. Thus the depth of cooking will determine how far denatured tissue 325 is from the imaging probe. In this tool, ratios of baseline to measured light are measured between different pairs of emitters and detectors, shown in the table in FIG. 7B. Measures between closely-spaced emitters and detectors yields information about shallow light paths that enter the tissue only shallowly from the imaging probe 300; information from widely spaced emitters and detectors measure tissue deeper and farther from the imaging probe 300. In the table in FIG. 7B, such measures are made at three different sizes of cooked tissue balls: no cooked tissue (at experiment start), small denatured tissue ball (at size shown as denatured tissue ball 325), and large denatured tissue ball that just touches the imaging probe (later in time, large denatured tissue ball not shown).

From visual inspection of the data, it can be seen that the ratios are larger when the emitter and detector are near the denatured tissue ball, and widely enough separated to detect the change in optical path due to the denatured tissue ball presence. Initially, there is no denatured tissue ball, so all of the calculations show cooked "NO" ("No ball" column). Later, there are some widely spaced emitters and detectors that detect the denatured tissue ball ("Small ball" column). Last, when the denatured tissue ball reaches the imaging probe, there are many cooked "YES" flags ("Large ball" column), and the location of the denatured tissue ball can be seen to be close to the space between emitter 323C and detector 324C, due to the "YES" in the narrowly separated pair. Thus, the device could now sound a warning alerting the user that the denatured tissue ball was about to cook structures next to the imaging probe at a specific location on the probe. It is possible that a cooling apparatus could be included to now cool this specific spot to prevent cooking, such as by allowing cold water to flow past this site. The cooked "YES" and "NO" data can be arranged in a table to make the image formation more apparent, as shown in FIG. 7C.

In this experiment, it can be seen that a depth of cooking can be calculated, as shown in the table in FIG. 7B. Another method to measure cooking would be to probe using only neighboring emitters and detectors, such that illumination and detection using neighboring emitters and detectors yields a probe mostly of local tissues. Also, the function of the above device would not change appreciably if there was provided only one emitter, and multiple detectors instead of one detector and multiple emitters.

Figure 8:
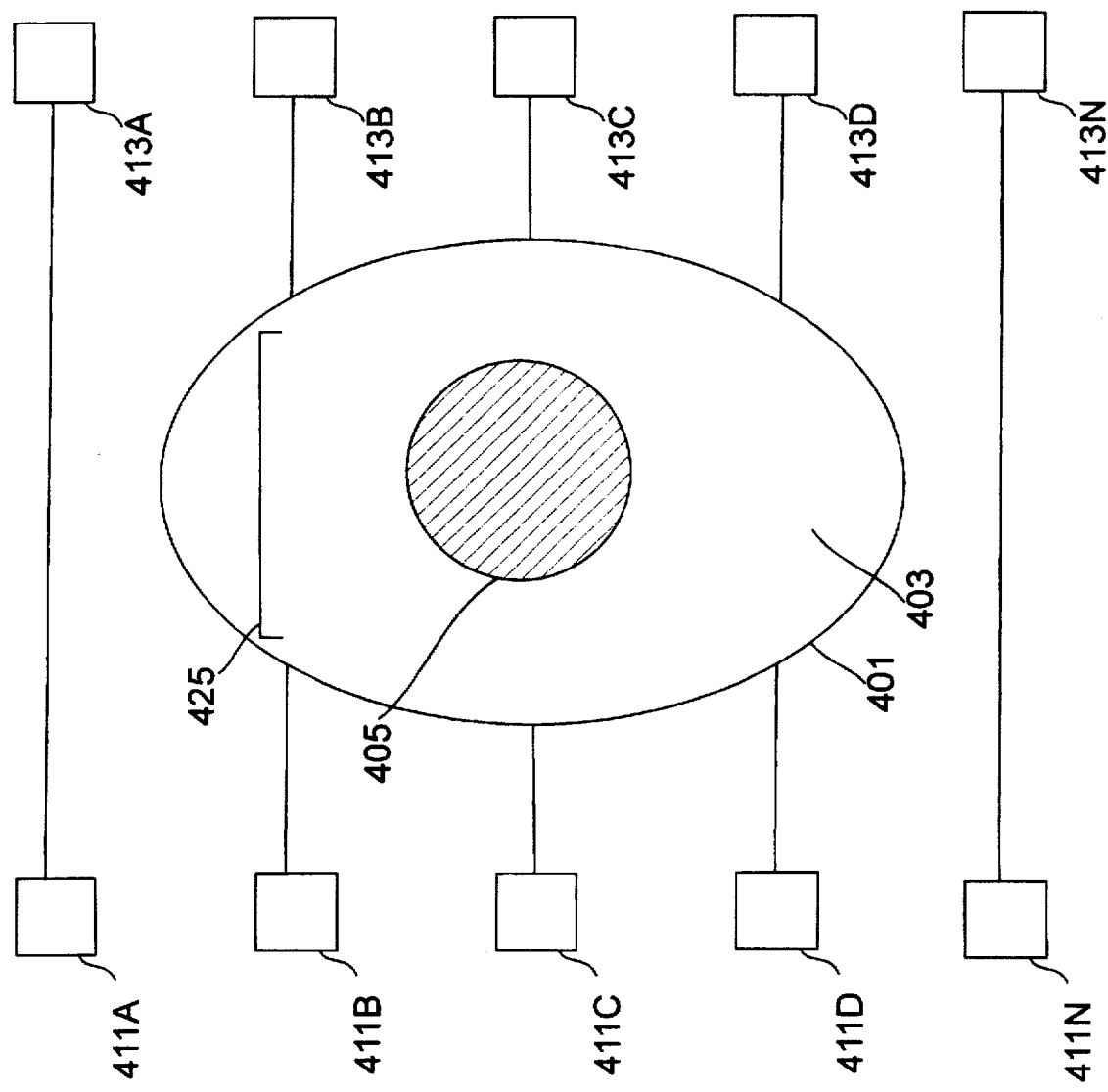
FIG. 8 illustrates a multiple detector smart tool for imaging tissue.
Figures 9A, 9B:
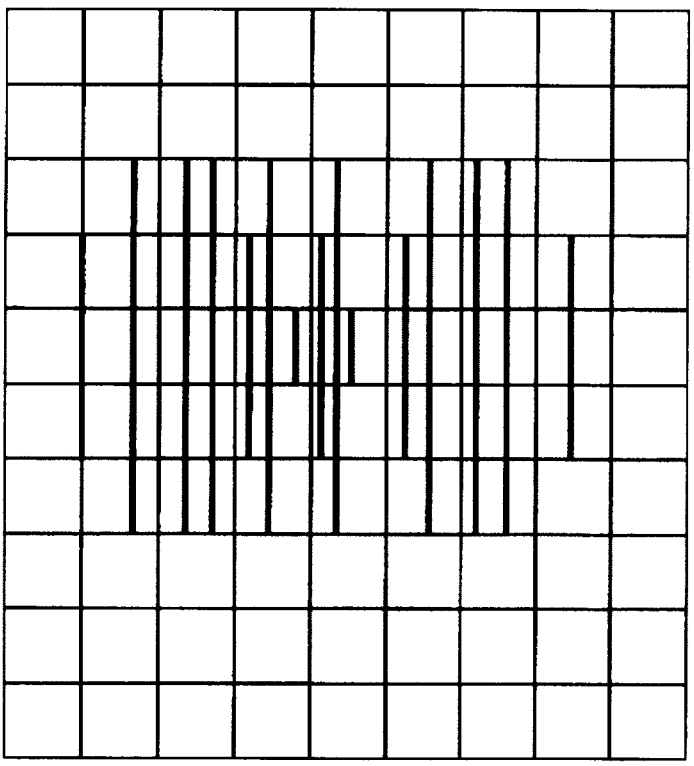
FIGS. 9A and 9B illustrate the formation of an image using the tool of FIG. 8.

Such a device could also be arranged to image. As shown in FIG. 8, tissue 401 is composed of uncooked region 403 and cooked region 405. Light from emitters 411 A–N could be detected by detectors 413A–N. With each detection, a measure of the thermal influence of the cooking upon the various regions between emitters and detectors could then be used to construct an image. For example, light from emitter 411A could be measured at 411B. From this measurement, an estimate of the percent of tissue cooked could be made. In this case, the light between emitter 411A and detector 413A does not pass through 401, while light from emitter 411B could be measured by detector 413B after passing through tissue region 425. All combinations of emitters and detectors could be measured, and emitters and detectors could be provided at right angles to those shown, in order to generate good coverage of the tissue. Analysis of the data could then be used to generate a table of the distribution of cooking, as shown in FIG. 9A, and this table could be used to form an image, as shown in FIG. 9B. Such an image could be formed by techniques reported by Benaron (*Science* (1993), Applied Optics (1994)), or by other methods, and the orientation of the emitters and detectors could vary in distribution and scanning patterns. In addition, spectroscopic analysis could yield improved images, without: violating the spirit of the invention.

One skilled in the art will appreciate that the present invention can be practiced by other than the described embodiments which are presented for proposed illustration and not of limitation.

We claim:

1. Apparatus for performing a thermal surgical intervention of tissue comprising:

a surgical tool to apply a thermal intervention on tissue and alter the tissue status;

an emitter of radiative energy of at least one frequency, at least a portion of said radiative energy being directed into said tissue, and said emitter being proximate said tool;

a detector responsive to a portion of radiative energy corresponding to said emitted radiative energy having traveled through at least a portion of said tissue, the detector having an output signal corresponding to said detected radiative energy, said detector being proximate said emitter; and a processor having an input operatively connected to said output signal and means for determining the status of said tissue portion as a result of said applied thermal intervention and to provide an indicator signal based upon said determined status, the processor being operatively connected to the surgical tool to control the operation of said surgical tool.

2. The apparatus of claim 1, wherein said emitter comprises a light source.

3. The apparatus of claim 1, wherein said emitter is selected from the group consisting of an ambient light source, an infrared light source, a laser, at least one LED, a fluorophore, a radio emitter, a radio wave source, and a self-emitting source.

4. The apparatus of claim 1, wherein said emitter comprises more than one source of radiative energy.

5. The apparatus of claim 1, wherein said detector comprises a light detector.

6. The apparatus of claim 5, wherein said light detector is selected from the group consisting of a photodiode, a phototransistor, an optical intensifier, a photomultiplier tube, a CCD element, a CCD array, and a phosphor screen.

7. The apparatus of claim 6, wherein said light detector is configured to be sensitive to the detection of radiative energy reaching said detector by a route selected from the group consisting of transmission, reflection, scattering, fluorescence, and reemission.

8. The apparatus of claim 1, wherein said detector comprises more than one detector, each detector having an output signal corresponding to said emitted radiative energy passing through different portions of tissue.

9. The apparatus of claim 1, wherein said processor further comprises means for comparing the detector output signal to a preselected criteria and determining whether the detector output corresponds to the preselected criteria.

10. The apparatus of claim 9 wherein the processor further comprises means for declaring a correspondence based on an algorithm, relating the detector output signal to the preselected criteria, selected from among the group consisting of class analysis, least-squares fitting, chemometrics, and partial component regression.

11. The apparatus of claim 1, wherein said processor determines the tissue status as at least a partial function of at least one preselected criterion selected from among the group consisting of absorbance, scattering, anisotropy factor, elastic scattering, polarization, fluorescence, temperature, and thermal diffusion.

12. The apparatus of claim 1, wherein said indicator signal is one of an optical signal, an auditory signal, a video overlay signal, an interlock trigger signal, and a tool control signal.

13. The apparatus of claim 1, wherein said indicator signal further comprises an image of the portion of tissue.

14. The apparatus of claim 1, wherein said surgical tool comprises an electrocautery device.

15. The apparatus of claim 14, wherein said electrocautery device comprises a bipolar electrocautery device.

16. The apparatus of claim 15, wherein the bipolar electrocautery device further comprises a pair of grasping members to engage tissue therebetween having mounted thereon said emitter of radiative energy and said detector in a tissue contacting surface of said grasping member.

17. The apparatus of claim 1, wherein said surgical tool comprises a laser beam.

18. The apparatus of claim 17, wherein said laser beam has a frequency that interacts with a component injected in the tissue to heat thermally said component.

19. The apparatus of claim 1, wherein said detector comprises multiple detectors and multiple emitters and said processing and sensing means further comprises means for operating said multiple emitters and detectors selectively to obtain a plurality of sensed output signals corresponding to a plurality of portions of tissue representing the status of the tissue portions.

20. The apparatus of claim 1, wherein at least one of said emitter and detector are mounted in a probe separate from such tool.

21. The apparatus of claim 1 wherein the surgical tool further comprises a tissue contacting surface and said emitter and detector are integrated into the surgical tool tissue contacting surface.

22. The apparatus of claim 1 wherein the surgical tool is operable to alter thermally said status of a first volume of tissue;

the light emitter comprises at least one light wavelength in the range of 0.2 to 10 microns, the light emitter being disposed to emit said at least one light wavelength into a second volume of tissue;

the light detector is positioned to detect at least a portion of radiative energy corresponding to said portion of emitted light which has traveled through a third volume of tissue, the third volume including at least a portion of the second volume, and at least a portion of the first volume; and the processor determines the status of at least one of the first, and second and third volumes of tissue related to said thermal alteration, said status changing as a direct result of said thermal intervention over time.

23. The apparatus of claim 22 wherein the surgical tool further comprises a laser beam.

24. The apparatus of claim 22 wherein the surgical tool further comprises an electrocautery electrode.

25. A system to assess changes in the status of tissue during a surgical thermal intervention, comprising:

a light emitter having at least one light wavelength of electromagnetic radiation in the range of 0.2 micron to 10 microns, the light emitter being disposed to emit said light into a first volume of tissue;

a light detector positioned to detect at least a portion of radiative energy corresponding to a portion of said emitted light which has traveled through a second volume of said tissue, the second volume including at least a portion of the first volume;

means for thermally altering at least one of the chemical and histological structure of a third volume of tissue, the third volume including at least a portion of the second volume; and means operatively connected to said light detector for determining, based upon said detected light portion, a status of at least one of said first, second and third volumes of tissue related to said thermal alteration, said status changing as a direct result of said thermal intervention over time.

26. The apparatus of claim 25, wherein said thermally altering means comprises an electrocautery tool.

27. The apparatus of claim 25, wherein said thermally altering means comprises a bipolar electrocautery tool.

28. The apparatus of claim 25, further comprising a grasper mechanism comprising a first member and a second member operatively arranged to hold the tissue therebetween proximately coupled to the light emitter and the light detector, and to maintain the tissue proximately coupled to said thermally altering means.

29. The apparatus of claim 28, wherein said grasper mechanism further comprises pressure control means for controllably varying a pressure exerted by the first and second members on said tissue.

30. The apparatus of claim 29, wherein said pressure control means operatively provides a compressive pressure over a range corresponding to a preselected weld strength.

31. The apparatus of claim 29, wherein said pressure control means operatively provides a compressive pressure over a range corresponding to a preselected vessel ablation.

32. The apparatus of claim 29, wherein said pressure control means comprises means to vary temporally the exerted pressure at a frequency and in a pressure range to assess the patency of blood flow in said held tissue.

33. The apparatus of claim 29, wherein said thermal altering means comprises a bipolar electrocautery tool, and wherein said grasper mechanism is operative to grasp and seal by electrocautery tissue and vessels larger than 3 to 5 millimeters in diameter.

34. The apparatus of claim 29, wherein said grasper mechanism further comprises a mirrored light integrating element located in at least one of the first and second member.

35. The apparatus of claim 34 wherein said grasper mechanism further comprises a fiber optic guide coupled to the emitter to transmit the emitted light to the tissue.

36. The apparatus of claim 33 wherein said grasper mechanism further comprises a non stick surface on each of the first and second members in contact with the tissue.

37. The apparatus of claim 25, further comprising feedback means for controlling the thermal altering means in response to said determined status.

38. The apparatus of claim 37 wherein the feedback means operates to reduce the extent of alteration of said tissue by thermally altering means in response to the said determined status corresponding to a predetermined criteria.

39. The apparatus of claim 38 wherein the feedback means modulates the thermal altering means operation.

40. A method to monitor the status of tissue during a surgical intervention comprising the steps of:
   a) emitting radiative energy of at least one wavelength into the tissue;
   b) detecting radiative energy corresponding to at least a portion of the emitted energy that has traveled through at least a portion of the tissue;
   c) altering at least one of the chemical and histological structure of at least one region of the tissue over time by applying a surgical intervention; and
   d) determining a change in status of the tissue in at least a portion of the one region in response to the surgical intervention, based upon the detected radiative energy.

41. The method of claim 40 wherein step c) further comprises applying a surgical intervention selected from the group consisting of cutting, stapling, cooking, welding, ablating, grasping, severing, mending, joining, sunctioning, drying, hydrating, aspirating, biopsying, suturing, irradiating, puncturing, and excising.

42. The method of claim 40 wherein step c) comprises thermally altering the tissue.

43. The method of claim 42 wherein the step of thermally altering the tissue includes applying heat to the tissue.

44. The method of claim 40, wherein step d) comprises collecting and averaging repeated measures of detected radiative energy over time.

45. The method of claim 40, wherein step d) comprises collecting and comparing repeated measures of detected radiative energy over time, said repeated measures being selected to provide a measure of change in tissue status over time.

46. The method of claim 40, wherein step d) further comprises obtaining a baseline measurement of the status of tissue from untreated tissue.

47. The method of claim 40, wherein the step of determining a change comprises the step of obtaining a baseline measurement of the status of tissue prior to performing step c).

48. The method of claim 40, wherein step d) further comprises comparing a measurement of detected radiative energy representative of a tissue state with at least one preselected criteria representative of a preselected tissue state.

49. The method of claim 40, wherein step d) further comprises collecting repeated measures of detected radiative energy over space.

50. The method of claim 45, wherein step d) further comprises forming an image of said portions of the one region of tissue in response to said collected repeated measures over space.

51. Apparatus to assess the status of tissue during a surgical intervention comprising:
   an emitter to emit radiative energy of at least one wavelength into said tissue;
   a detector to detect radiative energy corresponding to a portion of said emitted radiation after passing through at least a portion of said tissue, said detector being proximately coupled to said tissue;
   means, operatively coupled to said detector, for determining a status of tissue in real time as a function of a measure of said detected radiative energy and a predetermined criteria; and
   means responsive to said determining means for providing an output signal corresponding to said determined status.

52. The apparatus of claim 51, wherein said detector is adapted to be in contact with said tissue.

53. The apparatus of claim 52, wherein said detector is adapted to be invasively placed into said tissue.

54. The apparatus of claim 51 further comprising means responsive to said output control signal for providing a feedback control signal.

55. The apparatus of claim 51 wherein said emitter and detector further comprise more than one emitter and more than one detector and a controller to operate selectively said more than one emitter and detector to produce a plurality of measures of radiative energy corresponding to emitted radiation having different light paths through said tissue, wherein the determining means is responsive to said plurality of measures.

56. The apparatus of claim 55 wherein said determining means further comprises means for identifying changes in tissue status in response to said plurality of measures obtained over time.

57. The apparatus of claim 56 wherein said determining means further comprises means for identifying changes in tissue status in response to said plurality of measures obtained over space.

58. The apparatus of claim 56 wherein said determining means further comprises means for identifying changes in tissue status in response to said plurality of measures obtained over space and time.

59. The apparatus of claim 51 further comprising means to effect a surgical intervention.

60. The apparatus of claim 59 wherein said means to effect a surgical intervention comprises at least one tool selected from the group consisting of a cutting tool, a stapling tool, a cooking tool, a welding tool, an ablating tool, a grasping tool, a severing tool, a mending tool, a joining tool, a sanctioning tool, a drying tool, a hydrating tool, an aspirating tool, a biopsy tool, a suturing tool, an irradiating tool, a puncturing tool, and an excising tool.

61. The apparatus of claim 59 wherein the means to effect a surgical intervention has a variable performance and further comprises a control circuit means, responsive to the output signal, for varying the performance of the surgical intervention as a function of the determined tissue status.

62. The apparatus of claim 51 wherein the means for determining tissue status further includes at least one of a means for time-resolved, frequency-resolved, and multidetector spatially resolved movement.

* * * * *

UNITED STATES PATENT AND TRADEMARK OFFICE
CERTIFICATE OF CORRECTION

PATENT NO. : 5,762,609
DATED : June 9, 1998
INVENTOR(S) : Benaron et al..

It is certified that error appears in the above-identified patent and that said Letters Patent is hereby corrected as shown below:

Column 2, line 32, after "content" delete ":";
Column 5, line 6, after "without" delete ":";
Column 6, line 5, after "grossly to" delete "absorbetnce" and insert --absorbance--;
Column 8, line 62, after "devices" delete ";";
Column 12, line 8, after "coagulated" delete ".";
Column 12, line 64, after "tested" delete ",";
Column 13, line 15, after "thereof." delete "of" and insert --Of--;
Column 13, line 51, after "Dissection" delete ",Am" and insert --, Am--;
Column 13, line 53, after "Approach" delete ",Journal" and insert --, Journal--;
Column 14, line 23, after "259:146" delete ":";
Column 15, line 27, after "reduced" delete ".";
Column 18, line 51, after "used" delete "tc" and insert --to--;
Column 18, line 58, after "without" delete ":";

Signed and Sealed this

Fifteenth Day of June, 1999

Attest:

Q. TODD DICKINSON

Attesting Officer

Acting Commissioner of Patents and Trademarks